(12) United States Patent
Himmelsbach et al.

(10) Patent No.: US 8,399,461 B2
(45) Date of Patent: Mar. 19, 2013

(54) BICYCLIC HETEROCYCLES, MEDICAMENTS CONTAINING SAID COMPOUNDS, USE THEREOF, AND METHOD FOR PRODUCTION OF SAME

(75) Inventors: Frank Himmelsbach, Mittelbiberach (DE); Birgit Jung, Laupheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 601 days.

(21) Appl. No.: 12/513,731

(22) PCT Filed: Nov. 3, 2007

(86) PCT No.: PCT/EP2007/061842
§ 371 (c)(1),
(2), (4) Date: Jan. 5, 2010

(87) PCT Pub. No.: WO2008/055854
PCT Pub. Date: May 15, 2008

(65) Prior Publication Data
US 2011/0136805 A1 Jun. 9, 2011

(30) Foreign Application Priority Data
Nov. 10, 2006 (EP) .................... 06123820

(51) Int. Cl.
*A61K 31/517* (2006.01)
*A61K 31/5377* (2006.01)
*A61K 31/497* (2006.01)
*C07D 239/94* (2006.01)
*C07D 413/12* (2006.01)
*C07D 403/12* (2006.01)

(52) U.S. Cl. ............... 514/234.5; 514/266.2; 514/266.4; 544/293; 544/295; 544/357; 544/119

(58) Field of Classification Search .......... None
See application file for complete search history.

(56) References Cited

U.S. PATENT DOCUMENTS

| 3,985,749 A | 10/1976 | Foster |
| 4,322,420 A | 3/1982 | Kobayashi et al. |
| 4,335,127 A | 6/1982 | Vandenberk et al. |
| 4,640,920 A | 2/1987 | Boyle et al. |
| 4,845,629 A | 7/1989 | Murga |
| 4,921,863 A | 5/1990 | Sugimoto et al. |
| 5,064,833 A | 11/1991 | Ife et al. |
| 5,252,586 A | 10/1993 | Cain et al. |
| 5,457,105 A | 10/1995 | Barker |
| 5,616,582 A | 4/1997 | Barker |
| 5,642,285 A | 6/1997 | Woo et al. |
| 5,721,237 A | 2/1998 | Myers et al. |
| 5,747,498 A | 5/1998 | Schnur et al. |
| 5,760,041 A | 6/1998 | Wissner et al. |
| 5,770,599 A | 6/1998 | Gibson |
| 5,770,603 A | 6/1998 | Gibson |
| 5,821,246 A | 10/1998 | Brown et al. |
| 5,866,572 A | 2/1999 | Barker et al. |
| 5,929,080 A | 7/1999 | Frost |
| 5,938,706 A | 8/1999 | Feldman |
| 5,962,458 A | 10/1999 | Lohmann et al. |
| 6,004,967 A | 12/1999 | McMahon et al. |
| 6,046,206 A | 4/2000 | Pamukcu et al. |
| 6,117,433 A | 9/2000 | Edens et al. |
| 6,126,917 A | 10/2000 | Mishani et al. |
| 6,177,433 B1 | 1/2001 | Uckun et al. |
| 6,225,318 B1 | 5/2001 | Sobolov-Jaynes et al. |
| 6,270,747 B1 | 8/2001 | Nadel et al. |
| 6,297,258 B1 | 10/2001 | Wissner et al. |
| 6,313,130 B1 | 11/2001 | Uckun et al. |
| 6,326,373 B1 | 12/2001 | Uckun et al. |
| 6,362,336 B1 | 3/2002 | Lohmann et al. |

(Continued)

FOREIGN PATENT DOCUMENTS
CA 2417897 A1 1/2003
CA 2476008 A1 10/2003

(Continued)

OTHER PUBLICATIONS

International Search Report for PCT/EP2007/061842 mailed Apr. 10, 2008.

B.C. Baguley et al.: "Inhibition of growth of primary human tumor cell cultures by a 4-anilinoquinaziline inhibitor of the epidermal growth factor receptor family of tyrosine kinase", European Journal of Cancer, 1998, vol. 34, No. 7, pp. 1086-1090.

Ballard, Peter et al, "5-Substituted 4-anilinoquinazolines as potent, selective and orally active inhibitors of erbB2 receptor tyrosine kinase," Bioorganic & Medicinal Chemistry Letters 15(19):4226-4229 (2005).

(Continued)

*Primary Examiner* — Michael Barker
(74) *Attorney, Agent, or Firm* — Michael P. Morris; Edward S. Lazer

(57) ABSTRACT

The present invention relates to bicyclic heterocycles of general formula (I)

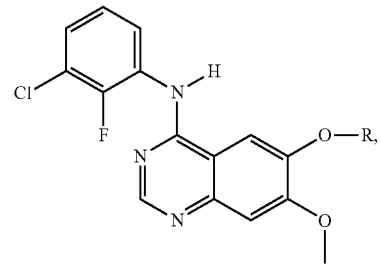

the tautomers, the stereoisomers, the mixtures and the salts thereof, particularly the physiologically acceptable salts thereof with inorganic or organic acids which have valuable pharmacological properties, particularly an inhibitory effect on signal transduction mediated by tyrosine kinases, the use thereof for treating diseases, particularly tumoral diseases, as well as benign prostatic hyperplasia (BPH), diseases of the lungs and respiratory tract, and the preparation thereof.

8 Claims, No Drawings

U.S. PATENT DOCUMENTS

| | | |
|---|---|---|
| 6,384,223 B1 | 5/2002 | Gletsos |
| 6,399,602 B1 | 6/2002 | Barker et al. |
| 6,403,580 B1 | 6/2002 | Himmelsbach et al. |
| 6,414,148 B1 | 7/2002 | Thomas et al. |
| 6,551,989 B2 | 4/2003 | Nadel et al. |
| 6,562,319 B2 | 5/2003 | Mishani et al. |
| 6,566,324 B2 | 5/2003 | Nadel et al. |
| 6,617,329 B2 | 9/2003 | Himmelsbach et al. |
| 6,627,634 B2 | 9/2003 | Himmelsbach et al. |
| 6,645,969 B1 | 11/2003 | Myers et al. |
| 6,653,305 B2 | 11/2003 | Himmelsbach et al. |
| 6,656,946 B2 | 12/2003 | Himmelsbach et al. |
| 6,740,651 B2 | 5/2004 | Himmelsbach et al. |
| 6,846,799 B1 | 1/2005 | Nadel et al. |
| 6,924,285 B2 | 8/2005 | Himmelsbach et al. |
| 6,972,288 B1 | 12/2005 | Himmelsbach et al. |
| 7,081,461 B1 | 7/2006 | Mortlock et al. |
| 7,119,084 B2 | 10/2006 | Himmelsbach et al. |
| 7,196,091 B2 | 3/2007 | Himmelsbach et al. |
| 7,354,894 B2 | 4/2008 | Nadel et al. |
| 7,358,222 B2 | 4/2008 | Nadel et al. |
| 7,456,189 B2 | 11/2008 | Himmelsbach et al. |
| 7,531,500 B2 | 5/2009 | Nadel et al. |
| 7,700,547 B2 | 4/2010 | Nadel et al. |
| 7,910,731 B2 | 3/2011 | Himmelsbach et al. |
| 7,998,949 B2 | 8/2011 | Himmelsbach et al. |
| 2001/0036919 A1 | 11/2001 | Nadel et al. |
| 2001/0041178 A1 | 11/2001 | Nadel et al. |
| 2001/0044435 A1 | 11/2001 | Himmelsbach et al. |
| 2002/0049197 A1 | 4/2002 | Himmelsbach et al. |
| 2002/0082270 A1 | 6/2002 | Himmelsbach et al. |
| 2002/0082271 A1 | 6/2002 | Himmelsbach et al. |
| 2002/0115675 A1 | 8/2002 | Himmelsbach et al. |
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0148990 A1 | 8/2003 | Nadel et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1* | 3/2004 | Himmelsbach et al. ... 514/266.2 |
| 2004/0176361 A1 | 9/2004 | Fujio et al. |
| 2004/0265302 A1 | 12/2004 | Nadel et al. |
| 2005/0014772 A1 | 1/2005 | Himmelsbach et al. |
| 2005/0059661 A1 | 3/2005 | Jung et al. |
| 2005/0070560 A1 | 3/2005 | Himmelsbach et al. |
| 2005/0159436 A1 | 7/2005 | Himmelsbach et al. |
| 2005/0165035 A1 | 7/2005 | Bradbury et al. |
| 2005/0182043 A1 | 8/2005 | Himmelsbach et al. |
| 2005/0215574 A1 | 9/2005 | Bradbury et al. |
| 2006/0063752 A1 | 3/2006 | Himmelsbach et al. |
| 2006/0264450 A1 | 11/2006 | Himmelsbach et al. |
| 2006/0270672 A1 | 11/2006 | Himmelsbach et al. |
| 2007/0135463 A1 | 6/2007 | Himmelsbach et al. |
| 2007/0270330 A1 | 11/2007 | Nadel et al. |
| 2008/0103161 A1 | 5/2008 | Himmelsbach et al. |
| 2008/0175797 A1 | 7/2008 | Nadel et al. |
| 2008/0199462 A1 | 8/2008 | Nadel et al. |
| 2009/0036676 A1 | 2/2009 | Himmelsbach et al. |
| 2009/0203683 A1 | 8/2009 | Himmelsbach et al. |
| 2009/0306072 A1 | 12/2009 | Jung et al. |
| 2009/0306105 A1 | 12/2009 | Himmelsbach et al. |
| 2010/0022505 A1 | 1/2010 | Himmelsbach et al. |
| 2010/0234371 A1 | 9/2010 | Himmelsbach et al. |
| 2011/0046148 A1 | 2/2011 | Himmelsbach et al. |
| 2011/0077246 A1 | 3/2011 | Himmelsbach et al. |
| 2011/0190248 A1 | 8/2011 | Himmelsbach et al. |

FOREIGN PATENT DOCUMENTS

| | | |
|---|---|---|
| CA | 2559699 A1 | 11/2005 |
| CA | 2559669 A1 | 3/2007 |
| CA | 2631813 A1 | 6/2007 |
| CA | 2669187 A1 | 5/2008 |
| DE | 10042058 A1 | 3/2002 |
| EP | 288563 A1 | 11/1988 |
| EP | 326330 A2 | 8/1989 |
| EP | 520722 A1 | 12/1992 |
| EP | 0566226 A1 | 10/1993 |
| EP | 602851 A1 | 6/1994 |
| EP | 607439 | 7/1994 |
| EP | 635507 A1 | 1/1995 |
| EP | 0787722 A1 | 8/1997 |
| EP | 837063 A1 | 4/1998 |
| EP | 1230919 A2 | 8/2002 |
| EP | 1283039 A1 | 2/2003 |
| EP | 1369418 A1 | 12/2003 |
| GB | 2033894 A | 5/1980 |
| GB | 2160201 A | 12/1985 |
| GB | 2295387 A | 5/1996 |
| JP | 11-189586 A | 7/1999 |
| WO | 88/02365 A1 | 4/1988 |
| WO | 92/14746 A1 | 9/1992 |
| WO | 92/20642 A1 | 11/1992 |
| WO | 93/08170 A1 | 4/1993 |
| WO | 93/17682 A1 | 9/1993 |
| WO | 94/27965 A1 | 12/1994 |
| WO | 95/00146 A1 | 1/1995 |
| WO | 95/03283 A1 | 2/1995 |
| WO | 95/15758 A1 | 6/1995 |
| WO | 95/19169 A2 | 7/1995 |
| WO | 95/24190 A2 | 9/1995 |
| WO | 96/15118 A1 | 5/1996 |
| WO | 96/16960 A1 | 6/1996 |
| WO | 96/09294 A1 | 9/1996 |
| WO | 96/30347 A1 | 10/1996 |
| WO | 96/33977 A1 | 10/1996 |
| WO | 96/33978 A1 | 10/1996 |
| WO | 96/33979 A1 | 10/1996 |
| WO | 96/33980 A1 | 10/1996 |
| WO | 96/33981 A1 | 10/1996 |
| WO | 96/39145 A1 | 12/1996 |
| WO | 97/03069 A1 | 1/1997 |
| WO | 97/11692 A2 | 4/1997 |
| WO | 97/18813 A1 | 5/1997 |
| WO | 97/22596 A1 | 6/1997 |
| WO | 97/30035 A1 | 8/1997 |
| WO | 97/30044 A1 | 8/1997 |
| WO | 9730034 | 8/1997 |
| WO | 97/32856 A1 | 9/1997 |
| WO | 97/38983 A1 | 10/1997 |
| WO | 97/38994 A1 | 10/1997 |
| WO | 97/42187 A1 | 11/1997 |
| WO | 98/02434 A1 | 1/1998 |
| WO | 98/13354 A1 | 4/1998 |
| WO | 98/19649 A2 | 5/1998 |
| WO | 98/38984 A2 | 9/1998 |
| WO | 98/43960 A1 | 10/1998 |
| WO | 98/50038 A1 | 11/1998 |
| WO | 98/50370 A1 | 11/1998 |
| WO | 99/01467 A2 | 1/1999 |
| WO | 99/06378 A1 | 2/1999 |
| WO | 99/06396 A1 | 2/1999 |
| WO | 99/09016 A1 | 2/1999 |
| WO | 99/10349 A1 | 3/1999 |
| WO | 99/24037 A1 | 5/1999 |
| WO | 99/35132 A1 | 7/1999 |
| WO | 99/61428 A1 | 12/1999 |
| WO | 00/00202 A1 | 1/2000 |
| WO | 00/06555 A1 | 2/2000 |
| WO | 00/09481 A1 | 2/2000 |
| WO | 00/10981 A1 | 3/2000 |
| WO | 00/12497 A2 | 3/2000 |
| WO | 00/18740 A1 | 4/2000 |
| WO | 00/20402 A1 | 4/2000 |
| WO | 00/24718 A1 | 5/2000 |
| WO | 00/44728 A1 | 8/2000 |
| WO | 00/47212 A1 | 8/2000 |
| WO | 00/51587 A2 | 9/2000 |
| WO | 00/51991 A1 | 9/2000 |
| WO | 00/55141 A1 | 9/2000 |
| WO | 00/55162 A2 | 9/2000 |
| WO | 00/56338 A1 | 9/2000 |
| WO | 00/56720 A1 | 9/2000 |
| WO | 00/68201 A1 | 11/2000 |

| | | | |
|---|---|---|---|
| WO | 00/68203 | A1 | 11/2000 |
| WO | 00/73260 | A1 | 12/2000 |
| WO | 00/78735 | A1 | 12/2000 |
| WO | 01/04102 | A1 | 1/2001 |
| WO | 01/07432 | A2 | 2/2001 |
| WO | 01/12227 | A1 | 2/2001 |
| WO | 01/21594 | A1 | 3/2001 |
| WO | 01/21595 | A1 | 3/2001 |
| WO | 01/21596 | A1 | 3/2001 |
| WO | 01/21597 | A1 | 3/2001 |
| WO | 01/32632 | A2 | 5/2001 |
| WO | 01/32651 | A1 | 5/2001 |
| WO | 01/45641 | A2 | 6/2001 |
| WO | 01/66099 | A2 | 9/2001 |
| WO | 01/76586 | A1 | 10/2001 |
| WO | 01/77085 | A1 | 10/2001 |
| WO | 01/77104 | A1 | 10/2001 |
| WO | 01/94341 | A1 | 12/2001 |
| WO | 01/98277 | A2 | 12/2001 |
| WO | 02/16352 | A1 | 2/2002 |
| WO | 02/18351 | A1 | 3/2002 |
| WO | 02/18370 | A1 | 3/2002 |
| WO | 02/18372 | A1 | 3/2002 |
| WO | 02/18373 | A1 | 3/2002 |
| WO | 02/18376 | A1 | 3/2002 |
| WO | 02/24684 | A1 | 3/2002 |
| WO | 02/30924 | A1 | 4/2002 |
| WO | 02/34711 | A1 | 5/2002 |
| WO | 02/34744 | A1 | 5/2002 |
| WO | 02/41882 | A2 | 5/2002 |
| WO | 02/44166 | A1 | 6/2002 |
| WO | 02/48117 | A1 | 6/2002 |
| WO | 02/50043 | A1 | 6/2002 |
| WO | 02/056882 | A1 | 7/2002 |
| WO | 02/062767 | A1 | 8/2002 |
| WO | 02/066445 | A1 | 8/2002 |
| WO | 02/068409 | A1 | 9/2002 |
| WO | 02/073235 | A2 | 9/2002 |
| WO | 02/076976 | A2 | 10/2002 |
| WO | 02/092577 | A1 | 11/2002 |
| WO | 02/092578 | A1 | 11/2002 |
| WO | 02/092579 | A1 | 11/2002 |
| WO | 02/094760 | A2 | 11/2002 |
| WO | 03/000188 | A2 | 1/2003 |
| WO | 03/040108 | A1 | 5/2003 |
| WO | 03/040109 | A2 | 5/2003 |
| WO | 03/045364 | A2 | 6/2003 |
| WO | 03/045395 | A1 | 6/2003 |
| WO | 03/049740 | A1 | 6/2003 |
| WO | 03/072539 | A1 | 9/2003 |
| WO | 03/082290 | A1 | 10/2003 |
| WO | 03/082831 | A1 | 10/2003 |
| WO | 2004/064718 | A2 | 8/2004 |
| WO | 2004/093880 | A1 | 11/2004 |
| WO | 2005/012290 | A1 | 2/2005 |
| WO | 2005/026151 | A1 | 3/2005 |
| WO | 2005/026152 | A1 | 3/2005 |
| WO | 2005/028469 | A1 | 3/2005 |
| WO | 2005/028470 | A1 | 3/2005 |
| WO | 2005/030757 | A1 | 4/2005 |
| WO | 2005/030765 | A1 | 4/2005 |
| WO | 2005/041973 | A1 | 5/2005 |
| WO | 2005/048928 | A2 | 6/2005 |
| WO | 2005/102349 | A1 | 11/2005 |
| WO | 2006/008173 | A2 | 1/2006 |
| WO | 2006/034015 | A1 | 3/2006 |
| WO | 2008/055854 | A1 | 5/2008 |

OTHER PUBLICATIONS

Ballard, Peter et al, "Inhibitors of epidermal growth factor receptor tyrosine kinase: Novel C-5 substituted anilinoquinazolines designed to target the ribose pocket," Bioorganic & Medicinal Chemistry Letters 16(6):1633-1637 (2006).

Ballard, Peter et al, "Inhibitors of epidermal growth factor receptor tyrosine kinase: Optimization of potency and in vivo pharmacokinetics," Bioorganic & Medicinal Chemistry Letters 16(18):4908-4912 (2006).

Barker et al., Studies Leading to the Identification of ZD1839 (IressaTM): An Orally Active, Selective Epidermal Growth Factor Receptor Tyrosine Kinase Inhibitor Targeted to the Treatment of Cancer, Bioorg. Med. Chem. Lett. 11(14): 1911-1914 (2001).

Boschelli, Diane H.; Small Molecule Inhibitors of Receptor Tyrosine Kinases; Review Article; Chemical Sciences (2001) pp. 1-35.

Bridges et al. (1996) "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor" J. Med. Chem.39: 267-276.

Chevalier et al. (1999) "Induction of DNA replication by peroxisome proliferators is independent of both tumour necrosis factor (alpha) priming and EGF-receptor tyrosine kinase activity" J. Cell Sci. 112(24): 4785-4791.

Communication from EPO dated Mar. 9, 2006, in EP Appln. No. 03 710 015.3, the European counterpart of the present application.

Communication from European Patent Office ("EPO") dated May 27, 2005, in EP Appln. No. 03 710 015.3, the European counterpart of the present application.

Communication from European Patent Office in EP Appln. No. 03 710 015.3, the European counterpart of the present application, dated Sep. 22, 2006.

Dahlin, Constance; Home HealthCare Nurse (2006) vol. 24, No. 3 pp. 148-55.

Denny et al., "Structure-Activity Relationships for 4-Anilinoquinazolines as Potent Inhibitors at the ATP Binding Site for the Epidermal Growth Factor Receptor in vitro," Clinical and Experimental Pharmacology and Physiology 23:424-427 (1996).

Drug Chemistry ed. E. Pawelczyk, PZWL, Wassaw, 1986, e.g. chapter 1.2.2.

English translation of Office Action in Chinese Patent Appln. No. 03811739.8, the Chinese counterpart of the present application, dated Jul. 21, 2006.

English Translation of Office Action in Japanese Patent Appln. No. 2003-580299, the Japanese counterpart of the present application, dated May 11, 2006.

English Translation of Response to Office Action in Chinese Patent Appln. No. 03811739.8, the Chinese counterpart of the present application, dated Dec. 5, 2006.

English translation of Response to Office Action in Japanese Patent Appln. No. 2003-580299, the Japanese counterpart of the present application, dated Jul. 28, 2006.

English Translation of Response to Office Action in Japanese Patent Appln. No. 2003-580299, the Japanese counterpart of the present application, dated Oct. 26, 2006.

Gazit et al. (1996) "Tyrophostins IV-Highly Potent Inhibitors . . . Relationship Study of 4-Anilidoquinazolines" Bioorganic & Medicinal Chemistry 4(8): 1203-1207.

Ghosh et al. (1999) "Structure-based design of potent inhibitors of EGF-receptor tyrosine kinase as anti-cancer agents" Anti-Cancer Drug Design 14, 403-410.

Gibson, K.H., et al.: "Epidermal growth factor receptor tyrosine kinase: Structure-activity relationships and antitumor activity of novel quinazolines", Bioorganic & Medicinal Chemistry Letters, 1997, vol. 7, No. 21, pp. 2723-2728.

Goldkorn, Tzipora, et al; EGF-Receptor Phosphorylation and Signaling Are Trageted by H2O2 Redox Stress; Am. J. Respir. Cell Mol. Biol (1998) vol. 19 pp. 786-798.

Harris, Craig et al, "Facile synthesis of 7-amino anilinoquinazolines via direct amination of the quinazoline core," Tetrahedron Letters 46(43):7381-7384 (2005).

Harris, Craig et al, "Selective alkylation of a 6,7-dihydroxyquinazoline," Tetrahedron Letters 46(45):7715-7719 (2005).

Hennequin et al. (1999) "Design and structure-activity relationship of a new class of potent VEGF receptor tyrosine kinaseinhibitors" J. Med. Chem. 42: 5369-5389.

Hennequin et al. (2002) "Novel 4-anilinoquinazolines with C-7 basic side chains. Design and structure activity relationship of a series of potent, orally active, VEGF receptor tyrosine kinase inhibitors" J. Med. Chem. 45: 1300-1312.

Hennequin, Laurent et al, "Novel 4-anilinoquinazolines with C-6 carbon-linked side Synthesis and structure-activity relationship of a series of potent, orally active, EGF receptor tyrosine kinase inhibitors," Bioorganic & Medicinal Chemistry Letters 16(10):2672-2676 (2006).

International Search Report for PCT/EP2004/010723 mailed Mar. 10, 2005.

International Search Report for PCT/EP2006/065000 mailed Feb. 6, 2007.

International Search Report for PCT/EP2006/068598 mailed Mar. 6, 2007.

International Search Report for PCT/EP2007/061355 mailed Jul. 15, 2008.

International Search Report for PCT/EP2008/051141 mailed Jul. 11, 2008.

International Search Report for PCT/EP2009/000805 mailed May 9, 2009.

International Search Report for PCT/EP2009/059510 mailed Sep. 18, 2009.

International Search Report for PCT/EP2009/059511 mailed Sep. 18, 2009.

International Search Report for PCT/EP2009/059519 mailed Sep. 18, 2009.

Rama Krishna Narla et al.: "4-(3'-Bromo-4'hyroxyphenyl)-amino-6,7-dimethoxyquinazoline: A novel quinazoline derivative with potent cytotoxic activity against human glioblastoma cells", Clinical cancer research,. Jun. 1998, vol. 4, pp. 1405-1414.

Reply to May 27, 2005, Communication from EPO dated Sep. 20, 2005.

International Search Report PCT/EP2003/03062 mailed Jun. 6, 2003.

International Search report, PCT/EP100/02228, Jul. 18, 2000.

International Search Report, Uae/P/209/2001, Apr. 20, 2010.

Kozielski, J; Polish Merkur Lekarski (2003) vol. 14, No. 4 p. 666-7.

Mendelsohn (2002) "Targeting the Epidermal Growth Factor Receptor for Cancer Therapy" Journal of Clinical Oncology 20(18s): 2s-13s.

Mendelsohn et al. (2003) "Status of Epidermal Growth Factor Receptor Antagonists in the Biology and Treatment of Cancer" Journal of Clinical Oncology 21(14): 2787-2799.

Myers et al. (1997) "The preparation and SAR of 4-(anilino), 4-(phenoxy), and 4-(thiophenoxy)-quinazolines: inhibitors of p56lck and EGF-R tyrosine kinase activity" Bioorg. Med. Chem. Lett. 7(4): 417-420.

Notices of Allowability and Allowance dated Jul. 26, 2006, in copending U.S. Appl. No. 10/857,342.

Office Action in Indian Patent Appln. No. 2630/DELNP/2004, the Indian counterpart of the present application, dated Apr. 20, 2006.

Pao et al. (2005) "Epidermal Growth Factor Receptor Mutations, Small-Molecule Kinase Inhibitors, and Non-Small-Cell Lung Cancer: Current Knowledge and Future Directions" Journal of Clinical Oncology 23(11):1-13.

Pending U.S. Appl. No. 11/487,727, filed Aug. 2, 2006.

Response to Office Action in Chinese Patent Appin. No. 03811739.8, the Chinese counterpart of the present application, dated Dec. 5, 2006.

Response to Office Action in Indian Patent Appin. No. 2630/DELNP/2004, the Indian counterpart of the present application, dated Jul. 24, 2006.

Response to Office Action in Japanese Patent Appln. No. 2003-580299, the Japanese counterpart of the present application, dated Jul. 28, 2006.

Rewcastle et al. (1995) "Tyrosine Kinase Inhibitors. 5 . . . 4-(Phenylamino)quinazolines as Potent . . . Inhibitors of the Tyrosine Kinase Domain of the Epidermal Growth Factor Receptor" J.Med. Chem. 38: 3482-3487.

Singh et al. (1998) "Inhibitors of the epidermal growth factor receptor protein tyrosine kinase: A quantitative structureactivity relationship analysis" J. Enzyme Inhibition 13: 125-134.

Smaill et al. (2000) "Tyrosine kinase inhibitors. 17. Irreversible inhibitors of the epidermalgrowth factor receptor: 4-(Phenylamino)quinazoline- and 4-(Phe-nylamino)pyrido" J Med Chem 43(16): 3199.

Stamos et al., "Structure of the Epidermal Growth Factor Receptor Kinase Domain Alone and in Complex with a 4-Anilinoquinazoline Inhibitor," J. Bio. Chem. 277(48):46265-46272 (2002).

Tang, Patricia, A., et al; A Review of Erlotinib and its Clinical Use; Expert OpinionPharmacotherapy (2006) vol. 7, No. 2 pp. 177-193.

Traxler, "Monthly Focus: Oncologic, Endocrine & Metabolic: Tyrosine kinase inhibitors in cancer treatment (Part II)," Expert Opinion on Therapeutic Patents 8:1599-1625 (1998).

Traxler, "Oncologic, Endocrine & Metabolic: Protein tyrosine kinase inhibitors in cancer treatment," Expert Opinion on Therapeutic Patents 7:571-588 (1997).

Tsou et al., "6- Substituted-4-(3-bromophenylamino)quinazolines As Putative Irreversible Inhibitors of the Epidermal Growth Factor Receptor (Egfr) and Human Epidermal Growth Factor Receptor (Her-2) Tyrosine Kinases with Enhanced Antitumor Activity," J. Med. Chem. 44:2719-2734 (2001).

Vema et al., "Design of EGFR Kinase Inhibitors: A Ligand-Based Approach and Its Confirmation with Structure-Based Studies," Bioorg. Med. Chem. 11:4643-4653 (2003).

Wright et al. (2001) "Allosteric inhibition of fructose-1,6-bisphosphatase by anilinoquinazolines" Bioorg Med Chem Lett. 11(1): 17-21.

* cited by examiner

BICYCLIC HETEROCYCLES, MEDICAMENTS CONTAINING SAID COMPOUNDS, USE THEREOF, AND METHOD FOR PRODUCTION OF SAME

This application is the national phase entry under 35 U.S.C. §371 of International Application No. PCT/EP2007/061842, filed Nov. 3, 2007, which claims priority to European Application No. 06123820.0, filed Nov. 10, 2006, each of which is hereby incorporated by reference in its entirety.

The present invention relates to bicyclic heterocycles of general formula

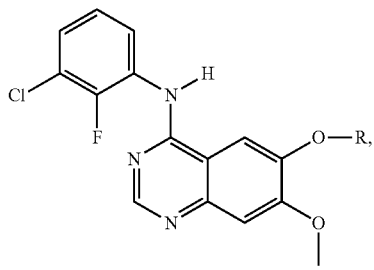

(I)

the tautomers, the stereoisomers, the mixtures and the salts thereof, particularly the physiologically acceptable salts thereof with inorganic or organic acids which have valuable pharmacological properties, particularly an inhibitory effect on signal transduction mediated by tyrosine kinases, the use thereof for treating diseases, particularly tumoral diseases, as well as benign prostatic hyperplasia (BPH), diseases of the lungs and respiratory tract, and the preparation thereof.

In the above general formula (I)
R denotes a group selected from among
cis-4-amino-cyclohexyl, trans-4-amino-cyclohexyl,
cis-4-methylamino-cyclohexyl, trans-4-methylamino-cyclohexyl,
cis-4-(methoxycarbonylamino)-cyclohexyl, trans-4-(methoxycarbonylamino)-cyclohexyl,
cis-4-(N-methoxycarbonyl-N-methyl-amino)-cyclohexyl, trans-4-(N-methoxycarbonyl-N-methyl-amino)-cyclohexyl,
cis-4-(ethyloxycarbonylamino)-cyclohexyl, trans-4-(ethyloxycarbonylamino)-cyclohexyl,
cis-4-(N-ethyloxycarbonyl-N-methyl-amino)-cyclohexyl, trans-4-(N-ethyloxycarbonyl-N-methyl-amino)-cyclohexyl,
cis-4-(tert.-butoxycarbonylamino)-cyclohexyl, trans-4-(tert.-butoxycarbonylamino)-cyclohexyl,
cis-4-(N-tert.-butoxycarbonyl-N-methyl-amino)-cyclohexyl, trans-4-(N-tert.-butoxycarbonyl-N-methyl-amino)-cyclohexyl,
cis-4-(acetylamino)-cyclohexyl, trans-4-(acetylamino)-cyclohexyl,
cis-4-(N-acetyl-N-methyl-amino)-cyclohexyl, trans-4-(N-acetyl-N-methyl-amino)-cyclohexyl,
cis-4-(methoxyacetyl-amino)-cyclohexyl, trans-4-(methoxyacetyl-amino)-cyclohexyl,
cis-4-(N-methoxyacetyl-N-methyl-amino)-cyclohexyl, trans-4-(N-methoxyacetyl-N-methyl-amino)-cyclohexyl,
cis-4-(dimethylaminocarbonyl-amino)-cyclohexyl, trans-4-(dimethylaminocarbonyl-amino)-cyclohexyl,
cis-4-(N-dimethylaminocarbonyl-N-methyl-amino)-cyclohexyl, trans-4-(N-dimethylaminocarbonyl-N-methyl-amino)-cyclohexyl,
cis-4-(morpholinocarbonyl-amino)-cyclohexyl, trans-4-(morpholinocarbonyl-amino)-cyclohexyl,
cis-4-(N-morpholinocarbonyl-N-methyl-amino)-cyclohexyl, trans-4-(N-morpholinocarbonyl-N-methyl-amino)-cyclohexyl,
cis-4-(piperazin-1-ylcarbonyl-amino)-cyclohexyl, trans-4-(piperazin-1-ylcarbonyl-amino)-cyclohexyl,
cis-4-(N-piperazin-1-ylcarbonyl-N-methyl-amino)-cyclohexyl, trans-4-(N-piperazin-1-ylcarbonyl-N-methyl-amino)-cyclohexyl,
cis-4-[(4-methyl-piperazin-1-ylcarbonyl)-amino]-cyclohexyl, trans-4-[(4-methyl-piperazin-1-ylcarbonyl)-amino]-cyclohexyl,
cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl,
cis-4-(methanesulphonylamino)-cyclohexyl, trans-4-(methanesulphonylamino)-cyclohexyl,
cis-4-(N-methanesulphonyl-N-methyl-amino)-cyclohexyl, trans-4-(N-methanesulphonyl-N-methyl-amino)-cyclohexyl,
cis-4-phthalimido-cyclohexyl and trans-4-phthalimido-cyclohexyl,
optionally in the form of the tautomers and mixtures thereof, and optionally the pharmacologically acceptable acid addition salts, solvates and hydrates thereof.

Preferred are compounds, in which
R denotes a group selected from among
cis-4-(methoxycarbonylamino)-cyclohexyl, trans-4-(methoxycarbonylamino)-cyclohexyl,
cis-4-(N-methoxycarbonyl-N-methyl-amino)-cyclohexyl, trans-4-(N-methoxycarbonyl-N-methyl-amino)-cyclohexyl,
cis-4-(ethyloxycarbonylamino)-cyclohexyl, trans-4-(ethyloxycarbonylamino)-cyclohexyl,
cis-4-(N-ethyloxycarbonyl-N-methyl-amino)-cyclohexyl, trans-4-(N-ethyloxycarbonyl-N-methyl-amino)-cyclohexyl,
cis-4-(tert.-butoxycarbonylamino)-cyclohexyl, trans-4-(tert.-butoxycarbonylamino)-cyclohexyl,
cis-4-(N-tert.-butoxycarbonyl-N-methyl-amino)-cyclohexyl, trans-4-(N-tert.-butoxycarbonyl-N-methyl-amino)-cyclohexyl,
cis-4-(methoxyacetyl-amino)-cyclohexyl, trans-4-(methoxyacetyl-amino)-cyclohexyl,
cis-4-(N-methoxyacetyl-N-methyl-amino)-cyclohexyl, trans-4-(N-methoxyacetyl-N-methyl-amino)-cyclohexyl,
cis-4-(dimethylaminocarbonyl-amino)-cyclohexyl, trans-4-(dimethylaminocarbonyl-amino)-cyclohexyl,
cis-4-(N-dimethylaminocarbonyl-N-methyl-amino)-cyclohexyl, trans-4-(N-dimethylaminocarbonyl-N-methyl-amino)-cyclohexyl,
cis-4-(morpholinocarbonyl-amino)-cyclohexyl, trans-4-(morpholinocarbonyl-amino)-cyclohexyl,
cis-4-(N-morpholinocarbonyl-N-methyl-amino)-cyclohexyl, trans-4-(N-morpholinocarbonyl-N-methyl-amino)-cyclohexyl,
cis-4-(piperazin-1-ylcarbonyl-amino)-cyclohexyl, trans-4-(piperazin-1-ylcarbonyl-amino)-cyclohexyl,
cis-4-(N-piperazin-1-ylcarbonyl-N-methyl-amino)-cyclohexyl, trans-4-(N-piperazin-1-ylcarbonyl-N-methyl-amino)-cyclohexyl,
cis-4-[(4-methyl-piperazin-1-ylcarbonyl)-amino]-cyclohexyl, trans-4-[(4-methyl-piperazin-1-ylcarbonyl)-amino]-cyclohexyl, cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl,
cis-4-(methanesulphonylamino)-cyclohexyl, trans-4-(methanesulphonylamino)-cyclohexyl,
cis-4-(N-methanesulphonyl-N-methyl-amino)-cyclohexyl, trans-4-(N-methanesulphonyl-N-methyl-amino)-cyclohexyl, cis-4-phthalimido-cyclohexyl and trans-4-phthalimido-cyclohexyl.

The compounds of general formula (I) may be prepared for example by the following methods:

a) reacting a compound of formula

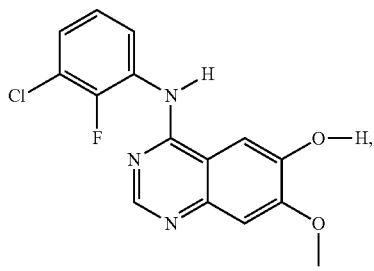

(II)

with a compound of general formula

Z¹—R (III), wherein

R is as hereinbefore defined and $Z^1$ denotes a leaving group such as a halogen atom, e.g. a chlorine or bromine atom, a sulphonyloxy group such as a methanesulphonyloxy or p-toluenesulphonyloxy group or a hydroxy group.

The reaction is conveniently carried out in a solvent such as ethanol, isopropanol, acetonitrile, toluene, tetrahydrofuran, dioxane, dimethylformamide, dimethylsulphoxide or N-methylpyrrolidinone, optionally in the presence of a base such as potassium carbonate or N-ethyl-diisopropylamine, at temperatures in the range from 20° C. to 160° C., preferably at temperatures in the range from 80° C. to 140° C.

With a compound of general formula (III) wherein $Z^1$ denotes a hydroxy group, the reaction is carried out in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycoldiethylether at temperatures in the range from −50 to 150° C., but preferably at temperatures in the range from −20 to 80° C.

b) reacting a compound of general formula (IV)

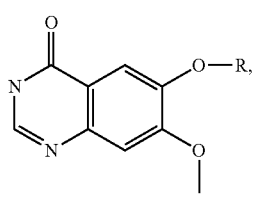

(IV)

wherein R is as hereinbefore defined, with a halogenating agent, for example an acid halide such as thionyl chloride, thionylbromide, phosphorus trichloride, phosphorus pentachloride or phosphorus oxychloride to form an intermediate compound of general formula (V),

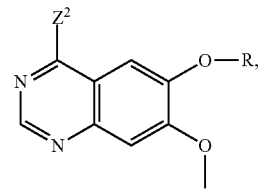

(V)

wherein R is as hereinbefore defined and $Z^2$ denotes a halogen atom such as a chlorine or bromine atom,
and subsequently reacting with 3-chloro-2-fluoro-aniline or the salts thereof.

The reaction with the halogenating agent is optionally carried out in a solvent such as methylene chloride, chloroform, acetonitrile or toluene and optionally in the presence of a base such as N,N-diethylaniline or N-ethyl-diisopropylamine at temperatures in the range from 20° C. to 160° C., preferably from 40° C. to 120° C. Preferably, however, the reaction is carried out with thionyl chloride and catalytic amounts of dimethylformamide at the boiling temperature of the reaction mixture.

The reaction of the compound of general formula (V) with 3-chloro-2-fluoro-aniline or the salts thereof is conveniently carried out in a solvent such as ethanol, isopropanol, acetonitrile, dioxane or dimethylformamide, optionally in the presence of a base such as potassium carbonate or N-ethyl-diisopropylamine, at temperatures in the range from 20° C. and 160° C., preferably from 60° C. to 120° C. Preferably, however, the reaction is carried out in isopropanol at the boiling temperature of the reaction mixture.

c) In order to prepare compounds of general formula (I) wherein R denotes a group selected from among cis-4-(methoxycarbonylamino)-cyclohexyl, trans-4-(methoxycarbonylamino)-cyclohexyl, cis-4-(N-methoxycarbonyl-N-methyl-amino)-cyclohexyl, trans-4-(N-methoxycarbonyl-N-methyl-amino)-cyclohexyl, cis-4-(ethyloxycarbonylamino)-cyclohexyl, trans-4-(ethyloxycarbonylamino)-cyclohexyl, cis-4-(N-ethyloxycarbonyl-N-methyl-amino)-cyclohexyl, trans-4-(N-ethyloxycarbonyl-N-methyl-amino)-cyclohexyl, cis-4-(tert.-butoxycarbonylamino)-cyclohexyl, trans-4-(tert.-butoxycarbonylamino)-cyclohexyl, cis-4-(N-tert.-butoxycarbonyl-N-methyl-amino)-cyclohexyl, trans-4-(N-tert.-butoxycarbonyl-N-methyl-amino)-cyclohexyl, cis-4-(acetylamino)-cyclohexyl, trans-4-(acetylamino)-cyclohexyl, cis-4-(N-acetyl-N-methyl-amino)-cyclohexyl, trans-4-(N-acetyl-N-methyl-amino)-cyclohexyl, cis-4-(methoxyacetyl-amino)-cyclohexyl, trans-4-(methoxyacetyl-amino)-cyclohexyl, cis-4-(N-methoxyacetyl-N-methyl-amino)-cyclohexyl, trans-4-(N-methoxyacetyl-N-methyl-amino)-cyclohexyl, cis-4-(dimethylaminocarbonyl-amino)-cyclohexyl, trans-4-(dimethylaminocarbonyl-amino)-cyclohexyl, cis-4-(N-dimethylaminocarbonyl-N-methyl-amino)-cyclohexyl, trans-4-(N-dimethylaminocarbonyl-N-methyl-amino)-cyclohexyl, cis-4-(morpholinocarbonyl-amino)-cyclohexyl, trans-4-(morpholinocarbonyl-amino)-cyclohexyl, cis-4-(N-morpholinocarbonyl-N-methyl-amino)-cyclohexyl, trans-4-(N-morpholinocarbonyl-N-methyl-amino)-cyclohexyl, cis-4-(piperazin-1-ylcarbonyl-amino)-cyclohexyl, trans-4-(piperazin-1-ylcarbonyl-amino)-cyclohexyl, cis-4-(N-piperazin-1-ylcarbonyl-N-methyl-amino)-cyclohexyl, trans-4-(N-piperazin-1-ylcarbonyl-N-methyl-amino)-cyclohexyl, cis-4-[(4-methyl-piperazin-1-ylcarbonyl)-amino]-cyclohexyl, trans-4-[(4-methyl-piperazin-1-ylcarbonyl)-amino]- cyclohexyl, cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl, cis-4-(methanesulphonylamino)-cyclohexyl, trans-4-(methanesulphonylamino)-cyclohexyl, cis-4-(N-methanesulphonyl-N-methyl-amino)-cyclohexyl and trans-4-(N-methanesulphonyl-N-methyl-amino)-cyclohexyl, reacting a compound of general formula (VI)

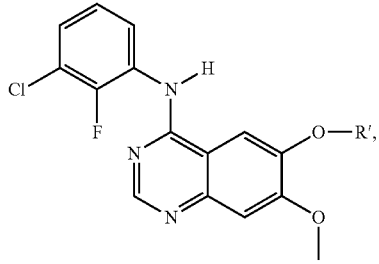

(VI)

wherein R' denotes a cis-4-amino-cyclohex-1-yl, trans-4-amino-cyclohex-1-yl, cis-4-(methylamino)-cyclohex-1-yl or trans-4-(methylamino)-cyclohex-1-yl group,
with a corresponding acylating agent such as methyl chloroformate, ethyl chloroformate, dimethylpyrocarbonate, diethyl pyrocarbonate, acetic anhydride, methoxyacetyl chloride, dimethylcarbamoyl chloride, morpholine-4-carbonyl chloride, 4-methyl-piperazin-1-yl-carbonyl chloride, 4-(tert-butyloxycarbonyl)-piperazin-1-yl-carbonyl chloride or methanesulphonyl chloride.

The reaction is conveniently carried out in a solvent such as methylene chloride, acetonitrile, toluene, tetrahydrofuran, dioxane, dimethylformamide, dimethylsulphoxide or N-methylpyrrolidinone, preferably in tetrahydrofuran or dioxane, optionally in the presence of a base such as potassium carbonate, sodium hydroxide solution or N-ethyl-diisopropylamine, at temperatures in the range from −20° C. to 80° C., preferably from 0° C. to 40° C.

d) In order to prepare compounds of general formula (I) wherein R denotes a cis-4-phthalimido-cyclohex-1-yl or trans-4-phthalimido-cyclohex-1-yl group, reacting a compound of general formula (VII)

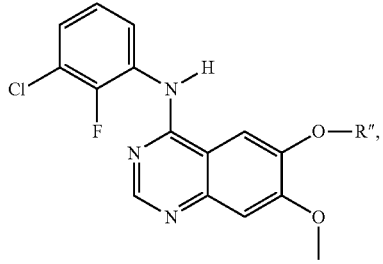

(VII)

wherein R" denotes a cis-4-amino-cyclohexyl or trans-4-amino-cyclohexyl group,
with phthalic anhydride or another reactive derivative of phthalic acid.

The reaction is conveniently carried out in a solvent such as acetic acid, acetonitrile, toluene, tetrahydrofuran, dioxane, dimethylformamide, dimethylsulphoxide or N-methylpyrrolidinone, preferably in acetic acid, optionally in the presence of a base such as potassium carbonate or N-ethyl-diisopropylamine, in a temperature range from 60° C. to 160° C., preferably from 80° C. to 120° C.

Preferably, however, the reaction is carried out in acetic acid at temperatures between 80° C. and 120° C.

In the reactions described hereinbefore, any reactive groups present such as amino, alkylamino or imino groups may be protected during the reaction by conventional protecting groups which are cleaved again after the reaction.

Protecting groups for an amino, alkylamino or imino group may be a formyl, acetyl, trifluoroacetyl, methoxycarbonyl, ethoxycarbonyl, tert. butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperature between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert. butyl or tert. butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran or methanol at temperatures between 0 and 50° C.

A methoxycarbonyl or ethoxycarbonyl group is preferably cleaved by treating with sodium hydroxide solution, optionally in the presence of a solvent such as tetrahydrofuran or methanol at temperatures between 0 and 50° C.

Moreover, the compounds of general formula I obtained may be resolved into their diastereomers, as mentioned hereinbefore. Thus, for example, cis/trans mixtures may be resolved by chromatography or crystallisation into their cis and trans isomers.

Moreover the compounds of formula (I) obtained may be converted into their salts, particularly for pharmaceutical use into the physiologically acceptable salts thereof with inorganic or organic acids. Examples of acids include hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae (II) to (VII) used as starting materials are known from the literature in some cases (e.g. from WO 03/82290 or WO 03/082831) or may be obtained using methods known from the literature (cf. Examples I to X), optionally with the additional inclusion of protective groups.

The compounds of general formula I according to the invention and the physiologically acceptable salts thereof have valuable pharmacological properties, in particular an inhibitory action on the signal transduction mediated by the epidermal growth factor receptor (EGF-R), and this can be caused, for example, by an inhibition of ligand binding, receptor dimerisation or tyrosine kinase itself. Moreover, it is possible that the signal transmission to components lying further downstream is blocked.

The biological properties of the novel compounds were tested as follows:

The inhibition of human EGF receptor kinase was determined with the aid of the cyto-plasmic tyrosine kinase domain (methionine 664 to alanine 1186 based on the sequence published in Nature 309 (1984), 418). For this, the protein was expressed in Sf9 insect cells as a GST fusion protein using the Baculovirus expression system.

The measurement of the enzyme activity was carried out in serial dilutions in the presence or absence of the test compounds. The polymer pEY (4:1) from SIGMA was used as a substrate. Biotinylated pEY (bio-pEY) was added as a tracer/substrate. Each 100 µl of reaction solution contained 10 µl of the inhibitor in 50% DMSO, 20 µl of the substrate solution (200 mM HEPES pH 7.4, 50 mM magnesium acetate, 2.5 mg/ml poly(EY), 5 µg/ml bio-pEY) and 20 µl of enzyme preparation. The enzyme reaction was started by addition of 50 µl of a 100 µM ATP solution in 10 mM magnesium chloride. The dilution of the enzyme preparation was adjusted such that the phosphate incorporation into the bio-pEY was linear with respect to time and amount of enzyme. The enzyme preparation was diluted in 20 mM HEPES pH 7.4, 1 mM EDTA, 130 mM sodium chloride, 0.05% Triton X-100, 1 mM DTT and 10% glycerol.

The enzyme assays were carried out at room temperature over a period of 30 minutes and ended by addition of 50 µl of a stop solution (250 mM EDTA in 20 mM HEPES pH 7.4). 100 µl were transferred to a streptavidin-coated microtitre plate and incubated at room temperature for 60 minutes. The plate was then washed with 200 µl of a wash solution (50 mM tris, 0.05% Tween 20). After addition of 100 µl of an HRPO-labelled anti-PY antibody (PY20H Anti-PTyr:HRP from Transduction Laboratories, 250 ng/ml) the mixture was incubated for 60 minutes. The microtitre plate was then washed three times with 200 µl each of wash solution. The samples were then treated with 100 µl of a TMB-peroxidase solution (A:B=1:1, Kirkegaard Perry Laboratories). The reaction was stopped after 10 minutes. The extinction was measured at $OD_{450nm}$ using an ELISA reader. All data points were determined as triplicates.

The data were fitted by means of an iterative calculation using an analysis program for sigmoidal curves (Graph Pad Prism Version 3.0) with a variable Hill pitch. All the iteration data released had a correlation coefficient of over 0.9 and the upper and lower values of the curves showed a spread of at least a factor of 5. From the curves, the active compound concentration was derived which inhibits the activity of the EGF receptor kinase to 50% ($IC_{50}$). The compounds according to the invention have $IC_{50}$ values of less than 100 µm. Preferably, the compounds according to the invention have $IC_{50}$ values of less than 1 µm.

The compounds of the general formula I according to the invention thus inhibit the signal transduction by tyrosine kinases, as demonstrated using the example of the human EGF receptor, and are therefore useful for the treatment of pathophysiological processes which are caused by hyperfunction of tyrosine kinases. These are, for example, benign or malignant tumours, in particular tumours of epithelial and neuroepithelial origin, formation of metastases and the abnormal proliferation of vascular endothelial cells (neoangiogenesis).

The compounds according to the invention are also useful for the prevention and treatment of diseases of the airways and of the lung which are accompanied by increased or altered mucus production, which is caused by stimulation of tyrosine kinases, such as, for example, in inflammatory diseases of the airways such as acute bronchitis, chronic bronchitis, chronic obstructive bronchitis (COPD), asthma, bronchiectases, allergic or non-allergic rhinitis or sinusitis, cystic fibrosis, α1-antitrypsin deficiency, or coughs, pulmonary emphysema, pulmonary fibrosis and hyperreactive airways, as well as acute and chronic diseases of the nasal mucosa and nasal sinuses, such as acute and chronic rhinitis, sinusitis and nasal polyps.

The compounds are also suitable for treating inflammatory diseases of the gastrointestinal tract and bile duct and gall bladder which are associated with disrupted activity of the tyrosine kinases, such as may be found e.g. In acute or chronic inflammatory changes such as cholecystitis, Crohn's disease, ulcerative colitis, and ulcers or polyposis in the gastrointestinal tract or such as may occur in diseases of the gastrointestinal tract which are associated with increased secretions, such as Ménétrier's disease, secreting adenomas or protein loss syndromes, and also for treating inflammatory diseases of the joints, such as rheumatoid arthritis, inflammatory diseases of the skin, the eyes, in inflammatory pseudopolyps, in colitis cystica profunda or pneumatosis cystoides intestinalis. The compounds may also be used for treating CNS and spinal cord injuries.

Preferred fields of application are inflammatory diseases of the respiratory organs or of the intestine, such as chronic bronchitis (COPD), chronic sinusitis, asthma, Crohn's disease, ulcerative colitis or polyposis of the intestines.

Particularly preferred fields of application are inflammatory diseases of the airways or lungs such as chronic bronchitis (COPD) or asthma or diseases of the nasal mucosa and sinus mucosa as well as nasal polyps.

Moreover, the compounds of general formula (I) and the physiologically acceptable salts thereof can be used for the treatment of other diseases caused by aberrant function of tyrosine kinases, such as, for example epidermal hyperproliferation (psoriasis), benign prostatic hyperplasia (BPH), inflammatory processes, diseases of the immune system, hyperproliferation in haematopoietic cells, the treatment of nasal polyps, etc.

On account of their biological properties, the compounds according to the invention can be used alone or in combination with other pharmacologically active compounds, for example in tumour therapy in monotherapy or in combination with other antitumour therapeutics, for example in combination with topoisomerase inhibitors (e.g. etoposide), mitosis inhibitors (e.g. vinblastine), compounds interacting with nucleic acids (e.g. cis-platin, cyclophosphamide, adriamycin), hormone antagonists (e.g. tamoxifen), inhibitors of metabolic processes (e.g. 5-FU etc.), cytokines (e.g. Interferons), antibodies etc. For the treatment of diseases in the region of the gastrointestinal tract, these compounds can likewise be given alone or in combination with motility- or secretion-influencing substances. These combinations can be administered either simultaneously or sequentially.

For the treatment of airway diseases, these compounds can be used alone or in combination with other airway therapeutics, such as, for example, compounds having secretolytic activity (e.g. ambroxol, N-acetylcysteine), broncholytic activity (e.g. tiotropium or ipratropium or fenoterol, salmeterol, salbutamol) and/or anti-inflammatory activity (e.g. theophylline or glucocorticoids).

Optionally the compounds of formula 1 may also be used in combination with W, wherein W denotes a pharmacologically active substance and is selected (for example) from among the betamimetics, anticholinergics, corticosteroids, PDE4-inhibitors, LTD4-receptor (cysLT1, cysLT2, cysLT3) antagonists, EGFR-inhibitors, dopamine-agonists, H1-antihistamines, PAF-antagonists, SYK-inhibitors, PDE3 inhibitors, lipoxin A4 derivatives, FPRL1 modulators, LTB4-receptor (BLT1, BLT2) antagonists, histamine H1 receptor antagonists, histamine H4 receptor antagonists, PI3 kinase inhibitors, inhibitors of non-receptor tyrosine kinases such as for example LYN, LCK, SYK, ZAP-70, FYN, BTK or ITK, inhibitors of MAP kinases such as for example p38, ERK1, ERK2, JNK1, JNK2, JNK3 or SAP, inhibitors of the NF-κB signal pathway such as for example IKK kinase inhibitors, iNOS inhibitors, MRP4 inhibitors, leukotriene biosynthesis inhibitors such as for example 5-lipoxygenase (5-LO) inhibitors, cPLA2 inhibitors, leukotriene A4 hydrolase inhibitors or FLAP inhibitors, non-steroidal anti-inflammatory agents (NSAIDs), CRTH2 antagonists, DP1-receptor modulators, thromboxane receptor antagonists, chemokine receptor antagonists of CCR1, CCR2, CCR2A, CCR2B, CCR4, CCR5, CCR6, CCR7, CCR8, CCR9, CCR10, CCR11, CXCR1, CXCR2, CXCR3, CXCR4, CXCR5, CXCR6, CX3CR1, neurokinin (NK1, NK2, NK3) antagonists, sphingosine 1-phosphate receptor modulators, modulators of adenosine receptors, modulators of purinergic receptors such as for example P2X7, histone deacetylase (HDAC) activators, bradykinin (BK1, BK2) antagonists, modulators of Calcitonin Gene Related Peptide (CGRP) such as e.g. CGRP antagonists, TACE inhibitors, mucoregulators, PPAR gamma agonists, Rho kinase inhibitors, interleukin 1-beta converting enzyme (ICE) inhibitors, toll-like receptor (TLR) modulators, HMG-CoA reductase inhibitors, VLA-4 antagonists, ICAM-1 inhibitors, SHIP agonists, TNFα antagonists, GABAa receptor antagonists, immunotherapeutics, modulators of the epithelial Na+ channel (ENaC) such as ENaC inhibitors, substances to counteract swelling of the airways and antitussive agents.

In addition, double or triple combinations of W may be combined with the compounds of formula 1. Combinations of W mentioned by way of example would include:

W denotes a betamimetic, combined with an anticholinergic, corticosteroid, PDE4-inhibitor, EGFR-inhibitor or LTD4-receptor antagonist, W denotes an anticholinergic, combined with a betamimetic, corticosteroid, PDE4-inhibitor, EGFR-inhibitor or LTD4-receptor antagonist, W denotes a corticosteroid, combined with a PDE4-inhibitor, EGFR-inhibitor or anticholinergic, W denotes a PDE4-inhibitor, combined with an EGFR-inhibitor or anticholinergic W denotes an EGFR-inhibitor, combined with an anticholinergic.

Examples of betamimetics preferably include compounds which are selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and
3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinolin-2-one
4-hydroxy-7-[2-{[2-{[3-(2-phenylethoxy)propyl] sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2.4.6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzenesulphonamide 3-(3-{7-[2-hydroxy-2-(4-hydroxy-3-hydroxymethyl-phenyl)-ethylamino]-heptyloxy}-propyl)-benzenesulphonamide
4-(2-{6-[4-(3-cyclopentanesulphonyl-phenyl)-butoxy]-hexylamino}-1-hydroxy-ethyl)-2-hydroxymethyl-phenol
N-adamantan-2-yl-2-(3-{2-[2-hydroxy-2-(4-hydroxy-3-hydroxymethyl-phenyl)-ethylamino]-propyl}-phenyl)-acetamide
(R,S)-4-(2-{[6-(2,2-difluoro-4-phenylbutoxy)hexyl]amino}-1-hydroxy-ethyl)-2-(hydroxymethyl)phenol
(R,S)-4-(2-{[6-(2,2-difluoro-2-phenylethoxy)hexyl]amino}-1-hydroxy-ethyl)-2-(hydroxymethyl)phenol
(R,S)-4-(2-{[4,4-difluoro-6-(4-phenylbutoxy)hexyl]amino}-1-hydroxy-ethyl)-2-(hydroxymethyl)phenol
(R,S)-4-(2-{[6-(4,4-difluoro-4-phenylbutoxy)hexyl]amino}-1-hydroxy-ethyl)-2-(hydroxymethyl)phenol
(R,S)-5-(2-{[6-(2,2-difluoro-2-phenylethoxy)hexyl]amino}-1-hydroxy-ethyl)-8-hydroxyquinolin-2(1H)-one
(R,S)-[2-({6-[2,2-difluoro-2-(3-methylphenyl)ethoxy]hexyl}amino)-1-hydroxyethyl]-2-(hydroxymethyl)phenol
4-(1R)-2-{[6-(2,2-difluoro-2-phenylethoxy)hexyl]amino}-1-hydroxyethyl)-2-(hydroxymethyl)phenol
(R,S)-2-(hydroxymethyl)-4-(1-hydroxy-2-{[4.4.5l5-tetrafluoro-6-(3-phenylpropoxy)hexyl]amino}ethyl)phenol
(R,S)-[5-(2-{[6-(2,2-difluoro-2-phenylethoxy)hexyl]amino}-1-hydroxy-ethyl)-2-hydroxyphenyl]formamide
(R,S)-4-[2-({6-[2-(3-bromophenyl)-2,2-difluoroethoxy]hexyl}amino)-1-hydroxyethyl]-2-(hydroxymethyl)phenol
(R,S)—N-[3-(1.1-difluoro-2-{[6-({2-hydroxy-2-[4-hydroxy-3-(hydroxymethyl)phenyl]-ethyl}amino)hexyl]oxy}ethyl)phenyl]urea
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione
(R,S)-4-[2-({6-[2,2-difluoro-2-(3-methoxyphenyl)ethoxy]hexyl}amino)-1-hydroxyethyl]-2-(hydroxymethyl)phenol
5-((1R)-2-{[6-(2,2-difluoro-2-phenylethoxy)hexyl]amino}-1-hydroxyethyl)-8-hydroxyquinolin-2(1H)-one
4-((1R)-2-{[4,4-difluoro-6-(4-phenylbutoxy)hexyl]amino}-1-hydroxy-ethyl)-2-(hydroxymethyl)phenol
(R,S)-4-(2-{[6-(3,3-difluoro-3-phenylpropoxy)hexyl]amino}-1-hydroxy ethyl)-2-(hydroxymethyl)phenol
(R,S)-(2-{[6-(2,2-difluoro-2-phenylethoxy)-4,4-difluorohexyl]amino}-1-hydroxyethyl)-2-(hydroxymethyl)phenol
(R,S)-4-(2-{[6-(2,2-difluoro-3-phenylpropoxy)hexyl]amino}-1-hydroxy-ethyl)-2-(hydroxymethyl)phenol
optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among: GSK233705B, GSK573719, AD-237, ALKS-27, LAS-34273, LAS-35201, CHF-5407, QAT-370 and tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from the salts of formula AC-1

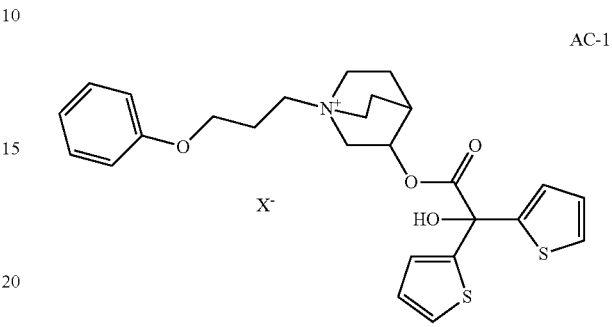

AC-1 wherein X⁻ denotes an anion with a single negative charge, preferably an anion selected from among fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among fluoride, chloride, bromide, methanesulphonate and p-toluenesulphonate, particularly preferably bromide, optionally in the form of the racemates, enantiomers or hydrates thereof. Of particular importance are those medicament combinations which contain the enantiomers of formula AC-1-en

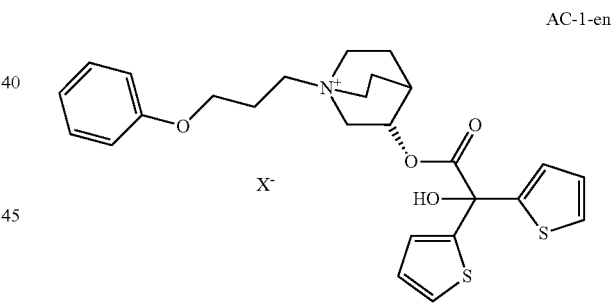

AC-1-en wherein X⁻ may have the meanings given above. Other preferred anticholinergics are selected from the salts of formula AC-2

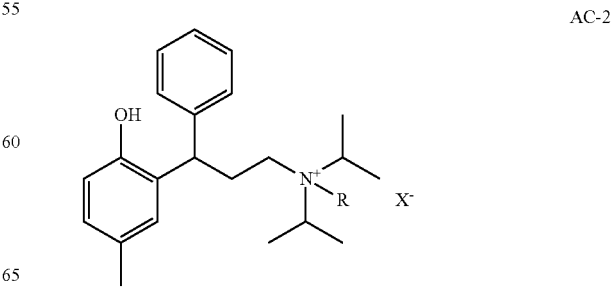

AC-2 wherein R denotes either methyl or ethyl and wherein X⁻ may have the meanings given above. In an alternative embodiment the compound of formula AC-2 may also be present in the form of the free base AC-2-base.

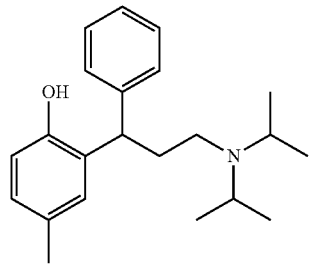

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide The above-mentioned compounds may also be used as salts within the scope of the present invention, while instead of the methobromide, the metho-X salts may be used wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, CP-4112, NCX-1020, NCX-1024, NS-126, PLD-177, PL-2146 QAE-397 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2.2.3.3-tetramethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, apremilast, arofyllin, atizoram, oglemilastum, tetomilast, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, GSK256066, ELB-353, ELB-526, GRC-4039, HT-0712, L-826141 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxyphenyl)-cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino-cyclohexan-1-yloxy}-7-methoxy-quinazoline 4-[(3-chloro-4-fluoro-phenyl)amino]-6-{trans-4-[(morpholin-4-yl)sulphonylamino-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonyl-methyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxyacetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine receptor agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among lexipafant and
4-(2-chlorophenyl)-9-methyl-2-[3(4-morpholinyl)-3-propanon-1-yl]-6H-thieno-[3,2-f]-[1,2,4]triazolo[4,3-a][1,4]diazepine
6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine
optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTB4-receptor antagonists used are preferably compounds selected from among AM-103, BIIL 284 and BIIL260, optionally in the form of the racemates, enantiomers, diastereomers thereof and optionally in the form of the pharmacologically acceptable acid addition salts, solvates, prodrugs or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-receptor antagonists used are preferably compounds selected from among montelukast, pranlukast, zafirlukast, MCC-847 (ZD-3523), MN-001, MEN-91507 (LM-1507), VUF-5078, VUF-K-8707, CR-3465, ONO-RS-531, L-733321, BAY-u9773 and
1-(((R)-(3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid,
optionally in the form of the racemates, enantiomers, diastereomers thereof and to optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4-receptor antagonists are optionally capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Histamine H1 receptor antagonists that may be used are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorophenoxamine, dimenhydrinate, diphenhydramine, promethazine, ebastine, olopatadine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists that may be used are preferably compounds selected from among: JNJ-7777120 optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Inhibitors of non-receptor tyrosine kinases that may be used such as for example LYN, LCK, SYK, ZAP-70, FYN, BTK or ITK are preferably compounds selected from among
2-[(2-aminoethyl)amino]-4-[(3-bromophenyl)amino]-5-pyrimidinecarboxamide;
2-[[7-(3,4-dimethoxyphenyl)imidazo[1,2-c]pyrimidin-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridin-5-yl]-1,3-propanediamine
7-(4-methoxyphenyl)-N-methyl-1,6-naphthyridin-5-amine;
N-[7-(4-methoxyphenyl)-1,6-naphthyridin-5-yl]-1,3-propanediamine;
N-[7-(2-thienyl)-1,6-naphthyridin-5-yl]-1,3-propanediamine;
N-[7-[4-(dimethylamino)phenyl]-1,6-naphthyridin-5-yl]-1,2-ethanediamine;
N-[7-(4-methoxyphenyl)-2-(trifluoromethyl)-1,6-naphthyridin-5-yl]-1,3-propanediamine;
N-[7-(4-methoxyphenyl)-3-phenyl-1,6-naphthyridin-5-yl]-1,3-propanediamine;
N-(7-phenyl-1,6-naphthyridin-5-yl)-1,3-propanediamine;
N-[7-(3-fluorophenyl)-1,6-naphthyridin-5-yl]-1,3-propanediamine;
N-[7-(3-chlorophenyl)-1,6-naphthyridin-5-yl]-1,3-propanediamine;
N-[7-[3-(trifluoromethoxy)phenyl]-1,6-naphthyridin-5yl]-1,3-propanediamine;
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;

N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]-N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]-1,2-cyclohexanediamine, optionally in the form of the racemates, enantiomers, diastereomers thereof and is optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

MAP kinase inhibitors used are preferably compounds selected from among: SCIO-323, SX-011, SD-282, SD-169, NPC-037282, SX-004, VX-702, GSK-681323, GSK-856553, ARRY-438162, ARRY-p38-002, ARRY-371797, AS-602801, AS-601245, AS-602183, CEP-1347, KC706, TA-5493, RO-6226, Ro-1487, SC-409 and BIRB-796, optionally in the form of the racemates, enantiomers, diastereomers thereof and optionally in the form of the pharmacologically acceptable acid addition salts, prodrugs, solvates or hydrates thereof.

Inhibitors of the NF-κB signal pathway or of the IKK kinases used are preferably compounds selected from among: MD-1041, MLN-041 and AVE-0547, optionally in the form of the racemates, enantiomers, diastereomers thereof and optionally in the form of the pharmacologically acceptable acid addition salts, prodrugs, solvates or hydrates thereof.

iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline, L-NA ($N^\omega$-nitro-L-arginine), L-NAME ($N^\omega$-nitro-L-argininemethylester), L-NMMA ($N^\omega$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51), 1400W, (S)-4-(2-acetimidoylamino-ethylsulphanyl)-2-amino-butyric acid (GW274150), 2-[2-(4-methoxy-pyridin-2-yl)-ethyl]-3H-imidazo[4,5-b]pyridine (BYK191023), 2-((R)-3-amino-1-phenyl-propoxy)-4-chloro-5-fluorobenzonitrile, 2-((1R,3S)-3-amino-4-hydroxy-1-thiazol-5-yl-butylsulphanyl)-6-trifluoromethyl-nicotinonitrile, 2-((1R,3S)-3-amino-4-hydroxy-1-thiazol-5-yl-butylsulphanyl)-4-chloro-benzonitrile, 2-((1R,3S)-3-amino-4-hydroxy-1-thiazol-5-yl-butylsulphanyl)-5-chloro-benzonitrile, (2S,4R)-2-amino-4-(2-chloro-5-trifluoromethyl-phenylsulphanyl)-4-thiazol-5-yl-butan-1-ol, 2-((1R,3S)-3-amino-4-hydroxy-1-thiazol-5-yl-butylsulphanyl)-5-chloro-nicotinonitrile, 4-((S)-3-amino-4-hydroxy-1-phenyl-butylsulphanyl)-6-methoxy-nicotinonitrile, substituted 3-phenyl-3,4-dihydro-1-isoquinolinamine such as e.g. AR-C102222, (1S,5S,6R)-7-chloro-5-methyl-2-aza-bicyclo[4.1.0]hept-2-en-3-ylamine (ONO-1714), (4R,5R)-5-ethyl-4-methyl-thiazolidin-2-ylideneamine, (4R,5R)-5-ethyl-4-methyl-selenazolidin-2-ylideneamine, 4-aminotetrahydrobiopterine, (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330), 3-(2,4-difluoro-phenyl)-6-[2-(4-imidazol-1-ylmethyl-phenoxy)-ethoxy]-2-phenyl-pyridine (PPA250), methyl 3-{[(benzo[1,3]dioxol-5-ylmethyl)-carbamoyl]-methyl}-4-(2-imidazol-1-yl-pyrimidin-4-yl)-piperazine-1-carboxylate (BBS-1), (R)-1-(2-imidazol-1-yl-6-methyl-pyrimidin-4-yl)-pyrrolidin-2-carboxylate (2-benzo[1,3]dioxol-5-yl-ethyl)-amide (BBS-2) and the pharmaceutical salts, prodrugs or solvates thereof.

As iNOS-inhibitors within the scope of the present invention it is also possible to use antisense oligonucleotides, particularly those antisense oligonucleotides that bind iNOS-coding nucleic acids. For example, WO 01/52902 describes antisense oligonucleotides, particularly antisense oligonucleotides that bind iNOS coding nucleic acids, for modulating the expression of iNOS.

MRP4-inhibitors used are preferably compounds selected from among N-acetyl-dinitrophenyl-cysteine, cGMP, cholates, diclofenac, dehydroepiandrosterone 3-glucuronide, dehydroepiandrosterone 3-sulphate, dilazep, dinitrophenyl-s-glutathione, estradiol 17-β-glucuronide, estradiol 3,17-disulphate, estradiol 3-glucuronide, estradiol 3-sulphate, estrone 3-sulphate, flurbiprofen, folate, n5-formyl-tetrahydrofolate, glycocholate, glycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[(3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulphinepyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers and diastereomers thereof and the pharmacologically acceptable acid addition salts and hydrates thereof. Particularly preferred are N-acetyl-dinitrophenyl-cysteine, dehydroepiandrosterone 3-sulphate, dilazep, dinitrophenyl-5-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers and diastereomers thereof and the pharmacologically acceptable acid addition salts and hydrates thereof.

The leukotriene biosynthesis inhibitors used such as for example those selected from among the 5-lipoxygenase (5-LO) inhibitors, cPLA2 inhibitors, leukotriene A4 hydrolase inhibitors or FLAP inhibitors, are preferably compounds selected from among zileuton, tipelukast, licofelone, darapladib, TA-270, IDEA-033, IDEA-070, NIK-639, ABT-761, fenleuton, tepoxalin, Abbott-79175, Abbott-85761, PLT-3514, CMI-903, PEP-03, CMI-977, MLN-977, CMI-947, LDP-977, efipladib, PLA-695, veliflapon, MK-591, MK-886 and BAYx1005, optionally in the form of the racemates, enantiomers and diastereomers thereof and optionally in the form of the pharmacologically acceptable acid addition salts, prodrugs, solvates or hydrates thereof.

Non-steroidal anti-inflammatories (NSAIDs) that may be used are preferably compounds selected from among piroxicam, diclofenac, naproxen, flurbiprofen, fenoprofen, ketoprofen and ibuprofen, nimesulide, indomethacin, sulindac, azapropazone, phenylbutazone, aspirin; meloxicam, celecoxib, rofecoxib, valdecoxib, lumarocoxib, parecoxib, tenoxicam and etoricoxib, optionally in the form of the racemates, enantiomers and diastereomers thereof and optionally in the form of the pharmacologically acceptable acid addition salts, prodrugs, solvates or hydrates thereof.

CRTH2 antagonists that may be used are preferably compounds selected from among ramatroban, AP-761, ODC-9101, SAR-398171, SAR-389644, laropiprant, TM-30642, TM-30643 and TM-30089, optionally in the form of the racemates, enantiomers and diastereomers thereof and optionally in the form of the pharmacologically acceptable acid addition salts, prodrugs, solvates or hydrates thereof.

DP1-receptor modulators that may be used are preferably compounds selected from among S-5751, laropiprant, SAR-389644 and TS-002, optionally in the form of the racemates, enantiomers and diastereomers thereof and optionally in the form of the pharmacologically acceptable acid addition salts, prodrugs, solvates or hydrates thereof.

Thromboxane receptor antagonists that may be used are preferably compounds selected from among seratrodast, BM-573, (+/−)-sodium[2-(4-chlorophenylsulphonylaminomethyl)-indan-5-yl]acetate monohydrate (Z-335) and KP-496, optionally in the form of the racemates, enantiomers and diastereomers thereof and optionally in the form of the pharmacologically acceptable acid addition salts, prodrugs, solvates or hydrates thereof.

Chemokine receptor antagonists that may be used are preferably compounds selected from among BX-471, SH-T-04268-H, MLN-3701, MLN-3897; MLX-010, MLX-025, MLX-011, MLX-031, MLX-045, AVE-0545, CP-481715, INCB-003284, INCB-8696, INCB-15050, INCB-9471, JNJ-27553292, Sch-417690, CCX-282, SB-656933, SCH-527123, SB-656933 and AMD-3100, optionally in the form of the racemates, enantiomers and diastereomers thereof and optionally in the form of the pharmacologically acceptable acid addition salts, prodrugs, solvates or hydrates thereof.

Neurokinin (NK1 or NK2) antagonists that may be used are preferably compounds selected from among: saredutant, nepadutant, PRX-96026 and figopitant, optionally in the form of the racemates, enantiomers and diastereomers thereof and optionally in the form of the pharmacologically acceptable acid addition salts, prodrugs, solvates or hydrates thereof.

Sphingosine1-phosphate receptor modulators that may be used are preferably compounds selected from among: c-6448 and FTY720, optionally in the form of the racemates, enantiomers and diastereomers thereof and optionally in the form of the pharmacologically acceptable acid addition salts, prodrugs, solvates or hydrates thereof.

Mucoregulators that may be used are preferably compounds selected from among: MSI-2216, erdosteine, fluorovent, talniflumate, INO-4995, BIO-11006, VR-496, fudosteine and ENAC blocker 552617, optionally in the form of the racemates, enantiomers and diastereomers thereof and optionally in the form of the pharmacologically acceptable acid addition salts, prodrugs, solvates or hydrates thereof.

PPAR gamma agonists that may be used are preferably compounds selected from among: rosiglitazone, ciglitazone, pioglitazone and SMP-028, optionally in the form of the racemates, enantiomers and diastereomers thereof and optionally in the form of the pharmacologically acceptable acid addition salts, prodrugs, solvates or hydrates thereof.

Rho kinase inhibitors that may be used are preferably compounds selected from among: fasudil, optionally in the form of the racemates, enantiomers and diastereomers thereof and optionally in the form of the pharmacologically acceptable acid addition salts, prodrugs, solvates or hydrates thereof.

Adenosine receptor modulators that may be used are preferably compounds selected from among CGH-2466, CVT-6883, MRS-1754, UK-432097 and L-971 optionally in the form of the racemates, enantiomers and diastereomers thereof and optionally in the form of the pharmacologically acceptable acid addition salts, prodrugs, solvates or hydrates thereof.

Bradykinin (BK2 or BK1) antagonists that may be used are preferably compounds selected from among icatibant and MEN-16132, optionally in the form of the racemates, enantiomers and diastereomers thereof and optionally in the form of the pharmacologically acceptable acid addition salts, prodrugs, solvates or hydrates thereof.

Endothelin antagonists that may be used are preferably compounds selected from among actelion-1, ambrisentan, sitaxsentan, TBC-3711, TBC-3214 and bosentan, optionally in the form of the racemates, enantiomers and diastereomers thereof and optionally in the form of the pharmacologically acceptable acid addition salts, prodrugs, solvates or hydrates thereof.

Interleukin 1-beta converting enzyme (ICE) inhibitors that may be used are preferably compounds selected from among pralnacasan, VRT-18858, RU-36384, VX-765 and VRT-43198, optionally in the form of the racemates, enantiomers and diastereomers thereof and optionally in the form of the pharmacologically acceptable acid addition salts, prodrugs, solvates or hydrates thereof.

Toll-like receptor (TLR) modulators that may be used are preferably compounds selected from among resiquimod, PF-3512676, AVE-0675, heplisav, IMO-2055, CpG-28, TAK-242, SAR-21609, RC-52743198 and 852A, optionally in the form of the racemates, enantiomers and diastereomers thereof and optionally in the form of the pharmacologically acceptable acid addition salts, prodrugs, solvates or hydrates thereof.

HMG-CoA Reductase inhibitors that may be used are preferably compounds selected from among lovastatin, simvastatin, pravastatin, fluvastatin and avorvastatin, optionally in the form of the racemates, enantiomers and diastereomers thereof and optionally in the form of the pharmacologically acceptable acid addition salts, prodrugs, solvates or hydrates thereof.

VLA-4 antagonists that may be used are preferably compounds selected from among natalizumab, valategrast, TBC-4746, CDP-323 and TL-1102, optionally in the form of the racemates, enantiomers and diastereomers thereof and optionally in the form of the pharmacologically acceptable acid addition salts, prodrugs, solvates or hydrates thereof.

ICAM-1 inhibitors that may be used are preferably compounds selected from among BIRT-2584, optionally in the form of the racemates, enantiomers and diastereomers thereof and optionally in the form of the pharmacologically acceptable acid addition salts, prodrugs, solvates or hydrates thereof.

SHIP agonists that may be used are preferably compounds selected from among AQX-MN100 and MN-106, optionally in the form of the racemates, enantiomers and diastereomers thereof and optionally in the form of the pharmacologically acceptable acid addition salts, prodrugs, solvates or hydrates thereof.

TNFα antagonists that may be used are preferably compounds selected from among infliximab, adalimumab, golimumab, cytofab and etanercept, optionally in the form of the racemates, enantiomers and diastereomers thereof and optionally in the form of the pharmacologically acceptable acid addition salts, prodrugs, solvates or hydrates thereof.

Substances to counter swelling of the airways that may be used are preferably compounds selected from among phenylephrine, phenylpropanolamine, pseudophedrine, oxymetazoline, epinephrine, naphazoline, xylometazoline, propylhexedrine and llevo-desoxyephedrine, optionally in the form of the racemates, enantiomers and diastereomers thereof and optionally in the form of the pharmacologically acceptable acid addition salts, prodrugs, solvates or hydrates thereof.

Antitussive substances that may be used are preferably compounds selected from among hydrocodone, caramiphen, carbetapentane and dextramethorphan, optionally in the form of the racemates, enantiomers and diastereomers thereof and optionally is in the form of the pharmacologically acceptable acid addition salts, prodrugs, solvates or hydrates thereof.

These compounds may be administered, either on their own or in combination with other active substances, by intravenous, subcutaneous, intramuscular, intraperitoneal or intranasal route, by inhalation or by transdermal or oral route, aerosol formulations being particularly suitable for inhalation.

For pharmaceutical administration the compounds according to the invention are generally used in doses of 0.001-100 mg/kg body weight, preferably 0.1-15 mg/kg, in warm-blooded vertebrates, particularly humans. For administration, they are incorporated together with one or more conventional inert carriers and/or diluents, e.g. with maize starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, to form conventional galenic preparations such as tablets, coated tablets, capsules, powders, suspensions, solutions, sprays or suppositories.

The following Examples are intended to illustrate the present invention without limiting it:

PREPARATION OF THE STARTING COMPOUNDS

Example I

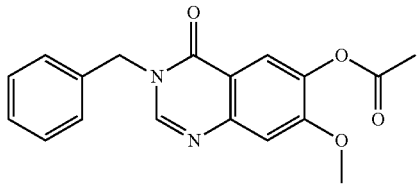 [SMILES: COc1cc2ncn(Cc3ccccc3)c(=O)c2cc1OC(C)=O]

3-Benzyl-3,4-dihydro-4-oxo-6-acetyloxy-7-methoxy-quinazoline 169 g of 3,4-dihydro-4-oxo-6-acetyloxy-7-methoxy-quinazoline, 118.8 ml benzylbromide and 138.2 g potassium carbonate are heated in 1600 ml acetone for 8 hours to 35-40° C. The mixture is stirred for 15 hours at ambient temperature and then combined with 2000 ml of water. The suspension is cooled to 0° C., the precipitate is suction filtered, washed with 400 ml of water and 400 ml tert.-butylmethylether and dried at 50° C. The solid is dissolved in 4000 ml methylene chloride, filtered and evaporated down. The residue is suspended in tert.-butylmethylether, suction filtered and dried at 50° C.

Yield: 203 g (86% of theory)
$R_f$ value: 0.80 (silica gel, methylene chloride/ethanol=9:1)
Mass spectrum (ESI$^+$): m/z=325 [M+H]$^+$

Example II

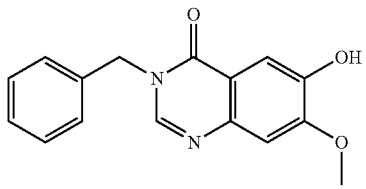 [SMILES: COc1cc2ncn(Cc3ccccc3)c(=O)c2cc1O]

3-Benzyl-3,4-dihydro-4-oxo-6-hydroxy-7-methoxy-quinazoline

Method A:

168.5 g of 6-hydroxy-7-methoxy-benzo[d][1,3]oxazin-4-one are dissolved in 1200 ml of toluene and 74.7 ml benzylamine are added. The mixture is refluxed for 15 hours and then cooled to ambient temperature. The precipitate is filtered off and washed with tert.-butylmethylether.

Yield 124 g (72% of theory)

Method B:

200 g of 3-benzyl-3,4-dihydro-4-oxo-6-acetyloxy-7-methoxy-quinazoline are suspended in 200 ml of water and 1000 ml of ethanol. 300 ml of 10N sodium hydroxide solution are added at ambient temperature and the mixture is heated to 30° C. for 1 hour. After the addition of 172 ml acetic acid and 2000 ml of water the mixture is stirred for 20 hours at ambient temperature. The precipitate is suction filtered, washed with water and acetone and dried at 60° C.

Yield: 172.2 g (98% of theory)
$R_f$ value: 0.25 (silica gel, methylene chloride/ethanol=19:1)
Mass spectrum (ESI$^+$): m/z=283 [M+H]$^+$

Example III

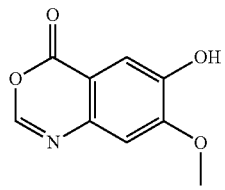

6-Hydroxy-7-methoxy-benzo[d][1,3]oxazin-4-one 1 g of 2-amino-5-hydroxy-4-methoxy-benzoic acid (prepared by reacting methyl 2-nitro-4,5-dimethoxy-benzoate with potassium hydroxide solution to form 2-nitro-5-hydroxy-4-methoxy-benzoic acid-potassium salt and subsequent catalytic hydrogenation in the presence of palladium on activated charcoal) and 20 ml triethyl orthoformate are heated to 100° C. for 2.5 hours. After cooling to ambient temperature the precipitate is suction filtered and washed with diethyl ether.

Yield: 0.97 g (93% of theory)
$R_f$ value: 0.86 (silica gel, methylene chloride/methanol/acetic acid=90:10:1)
Mass spectrum (ESI$^+$): m/z=194 [M+H]$^+$

Example IV

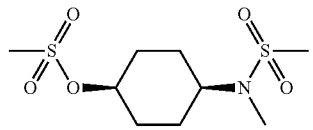

cis-1-(methanesulphonyloxy)-4-(N-methanesulphonyl-N-methyl-amino)-cyclohexane

Prepared by reacting cis-1-hydroxy-4-methylamino-cyclohexane with methanesulphonic acid chloride in tetrahydrofuran in the presence of triethylamine.

Mass spectrum (ESI$^+$): m/z=286 [M+H]$^+$

The following may be obtained analogously to Example IV:

| Example | Structure |
|---|---|
| IV(1) | CH₃SO₂-O-cyclohexyl-N(CH₃)-C(O)-O-ethyl |
| IV(2) | CH₃SO₂-O-cyclohexyl-N(CH₃)-C(O)-O-methyl |
| IV(3) | CH₃SO₂-O-cyclohexyl-N(CH₃)-C(O)-O-ethyl |
| IV(4) | CH₃SO₂-O-cyclohexyl-N(CH₃)-C(O)-O-methyl |
| IV(5) | CH₃SO₂-O-cyclohexyl-phthalimide |
| IV(6) | CH₃SO₂-O-cyclohexyl-phthalimide |
| IV(7) | CH₃SO₂-O-cyclohexyl-N(CH₃)-S(O)₂-CH₃ |
| IV(8) | CH₃SO₂-O-cyclohexyl-N(CH₃)-C(O)-O-tBu |

Mass spectrum (ESI⁺): m/z = 308 [M + H]⁺

| Example | Structure |
|---|---|
| IV(9) | CH₃SO₂-O-cyclohexyl-N(CH₃)-C(O)-O-tBu |

Mass spectrum (ESI⁺): m/z = 308 [M + H]⁺

| IV(10) | CH₃SO₂-O-cyclohexyl-N(CH₃)-C(O)-CH₃ |
| IV(11) | CH₃SO₂-O-cyclohexyl-N(CH₃)-C(O)-CH₂-O-CH₃ |
| IV(12) | CH₃SO₂-O-cyclohexyl-N(CH₃)-C(O)-CH₃ |
| IV(13) | CH₃SO₂-O-cyclohexyl-N(CH₃)-C(O)-CH₂-O-CH₃ |
| IV(14) | Tol-SO₂-O-cyclohexyl-N(CH₃)-C(O)-O-tBu |

Mass spectrum (ESI⁺): m/z = 401 [M + NH₄]⁺

| IV(15) | Tol-SO₂-O-cyclohexyl-NH-C(O)-O-tBu |

Mass spectrum (ESI⁺): m/z = 370 [M + H]⁺

| IV(16) | Tol-SO₂-O-cyclohexyl-NH-C(O)-O-tBu |

Mass spectrum (ESI⁺): m/z = 387 [M + NH₄]⁺

Example V

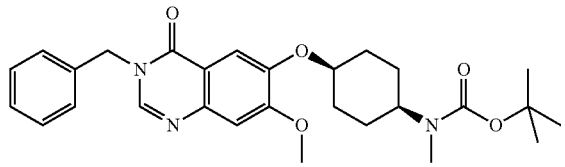 [SMILES: COc1cc2ncn(Cc3ccccc3)c(=O)c2cc1O[C@H]1CC[C@@H](N(C)C(=O)OC(C)(C)C)CC1]

3-Benzyl-3,4-dihydro-4-oxo-6-{cis-4-[N-(tert-butyloxycarbonyl)-N-methyl-amino]-cyclohexyl-oxy}-7-methoxy-quinazoline Prepared by reacting 4 g 3-benzyl-3,4-dihydro-4-oxo-6-hydroxy-7-methoxy-quinazoline and 8.77 g cis-1-methanesulphonyloxy-4-[N-(tert-butyloxycarbonyl)-N-methyl-amino]-cyclohexane in the presence of 4.33 g potassium carbonate in 32 ml N-methyl-pyrrolidinone at 100-120° C.

$R_f$ value: 0.78 (silica gel; ethyl acetate/methanol=95:5)
Mass spectrum (ESI$^+$): m/z=494 [M+H]$^+$ The following may be obtained analogously to Example V:

| Example | Structure |
| --- | --- |
| V(1) | 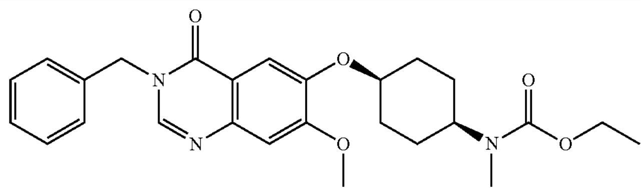 [SMILES: CCOC(=O)N(C)[C@H]1CC[C@@H](Oc2cc3c(=O)n(Cc4ccccc4)cnc3cc2OC)CC1] |
| V(2) | 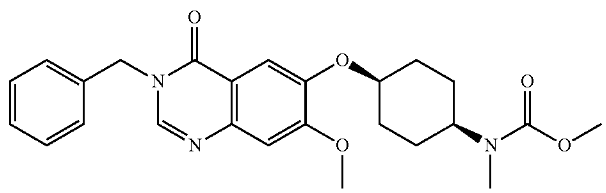 [SMILES: COC(=O)N(C)[C@H]1CC[C@@H](Oc2cc3c(=O)n(Cc4ccccc4)cnc3cc2OC)CC1] |
| V(3) | 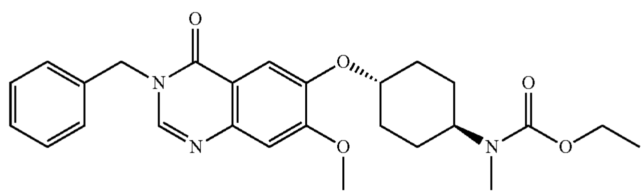 [SMILES: CCOC(=O)N(C)[C@H]1CC[C@H](Oc2cc3c(=O)n(Cc4ccccc4)cnc3cc2OC)CC1] |
| V(4) | 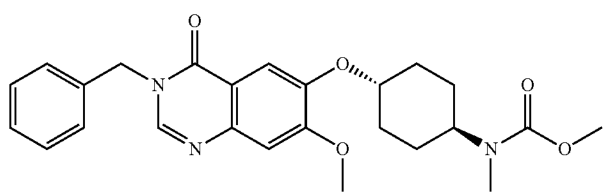 [SMILES: COC(=O)N(C)[C@H]1CC[C@H](Oc2cc3c(=O)n(Cc4ccccc4)cnc3cc2OC)CC1] |
| V(5) | 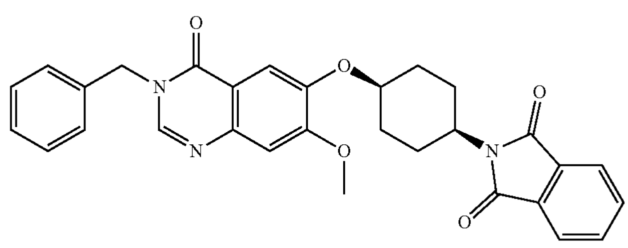 [SMILES: COc1cc2ncn(Cc3ccccc3)c(=O)c2cc1O[C@H]1CC[C@@H](N2C(=O)c3ccccc3C2=O)CC1] |
| V(6) | 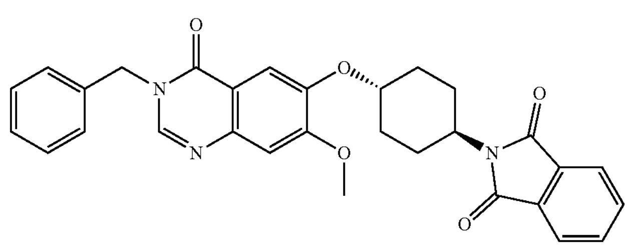 [SMILES: COc1cc2ncn(Cc3ccccc3)c(=O)c2cc1O[C@H]1CC[C@H](N2C(=O)c3ccccc3C2=O)CC1] |

| Example | Structure |
|---------|-----------|
| V(7) | *(structure)* |
| V(8) | *(structure)* |
| V(9) | *(structure)* |
| V(10) | *(structure)* |
| V(11) | *(structure)* |
| V(12) | *(structure)* |
| V(13) | *(structure)* |

Example VI

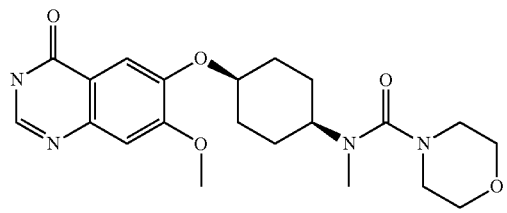

3,4-Dihydro-4-oxo-6-[cis-4-(N-morpholinocarbonyl-N-methyl-amino)-cyclohexyl-oxy]-7-methoxy-quinazoline A mixture of 1.4 g 3-benzyl-3,4-dihydro-4-oxo-6-[cis-4-(N-morpholinocarbonyl-N-methyl-amino)-cyclohexyl-oxy]-7-methoxy-quinazoline and 20 ml glacial acetic acid is hydrogenated in the presence of 0.3 g palladium on activated charcoal (10% Pd) at 80° C. under a hydrogen pressure of 50 psi until the reaction is complete. The catalyst is suction filtered, the filtrate is evaporated to dryness and combined with 15 ml of ethyl acetate. The precipitate is suction filtered, washed with 5 ml of ethyl acetate and dried.

Yield: 0.8 g (70% of theory)

$R_f$-value: 0.40 (silica gel, methylene chloride/methanol=9:1)

Mass spectrum (ESI$^+$): m/z=417 [M+H]$^+$

The following may be obtained analogously to Example VI:

| Example | Structure |
|---|---|
| VI(1) | 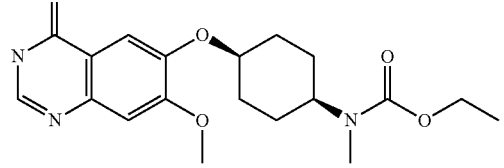 |
| VI(2) | 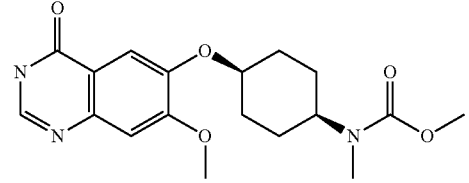 [SMILES: COC(=O)N(C)[C@H]1CC[C@@H](Oc2cc3c(=O)[nH]cnc3cc2OC)CC1] |
| VI(3) | 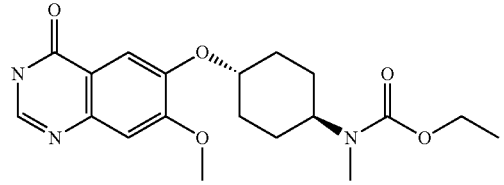 [SMILES: CCOC(=O)N(C)[C@H]1CC[C@H](Oc2cc3c(=O)[nH]cnc3cc2OC)CC1] |
| VI(4) | 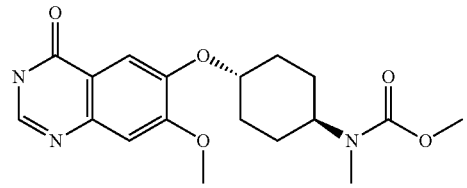 [SMILES: COC(=O)N(C)[C@H]1CC[C@H](Oc2cc3c(=O)[nH]cnc3cc2OC)CC1] |
| VI(5) | 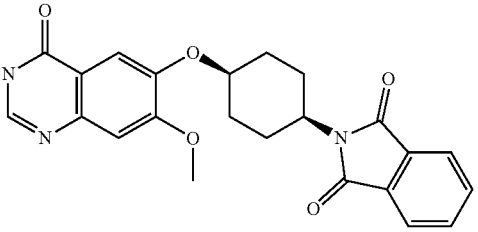 [SMILES: COc1cc2nc[nH]c(=O)c2cc1O[C@H]1CC[C@@H](N2C(=O)c3ccccc3C2=O)CC1] |
| VI(6) | 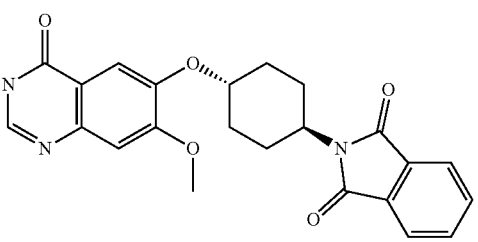 [SMILES: COc1cc2nc[nH]c(=O)c2cc1O[C@H]1CC[C@H](N2C(=O)c3ccccc3C2=O)CC1] |
| VI(7) | 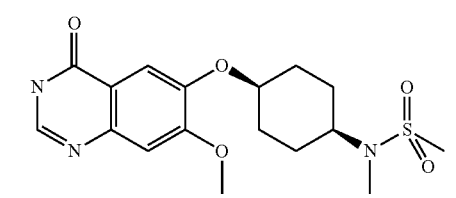 [SMILES: COc1cc2nc[nH]c(=O)c2cc1O[C@H]1CC[C@@H](N(C)S(C)(=O)=O)CC1] |
| VI(8) | 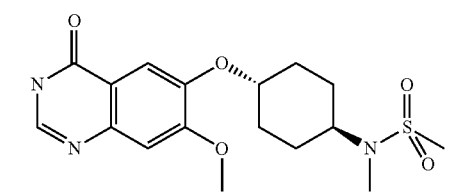 [SMILES: COc1cc2nc[nH]c(=O)c2cc1O[C@H]1CC[C@H](N(C)S(C)(=O)=O)CC1] |
| VI(9) | 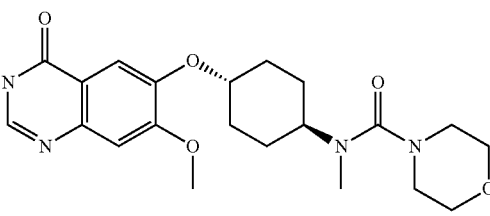 |
| VI(10) | 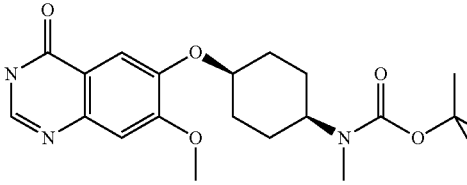 |

Example VII

4-Chloro-6-[cis-4-(N-morpholinocarbonyl-N-methyl-amino)-cyclohexyl-oxy]-7-methoxy-quinazoline-hydrochloride 800 mg of 3,4-dihydro-4-oxo-6-[cis-4-(N-morpholinocarbonyl-N-methyl-amino)-cyclohexyl-oxy]-7-methoxy-quinazoline, 7 ml of thionyl chloride and 0.1 ml dimethylformamide are refluxed for 3 hours. The volatile components of the reaction mixture are eliminated using the rotary evaporator, the residue is combined with toluene and concentrated again by rotary evaporation.

Mass spectrum (ESI$^+$): m/z=435, 437 [M+H]$^+$

The free base may also be obtained by alkaline working up.

The following may be obtained analogously to Example VII:

| Example | Structure |
|---|---|
| VII(5) | (4-chloro-6-methoxyquinazolinyl-oxy-cyclohexyl-phthalimide) xHCl |
| VII(6) | (4-chloro-6-methoxyquinazolinyl-oxy-cyclohexyl-phthalimide) xHCl |
| VII(7) | (4-chloro-6-methoxyquinazolinyl-oxy-cyclohexyl-N-methyl-methanesulfonamide) xHCl |
| VII(8) | (4-chloro-6-methoxyquinazolinyl-oxy-cyclohexyl-N-methyl-methanesulfonamide) xHCl |
| VII(9) | (4-chloro-6-methoxyquinazolinyl-oxy-cyclohexyl-N-methyl-morpholinocarboxamide) xHCl |
| VII(10) | (4-chloro-6-methoxyquinazolinyl-oxy-cyclohexyl-N-methyl-acetamide) xHCl |
| VII(11) | (4-chloro-6-methoxyquinazolinyl-oxy-cyclohexyl-N-methyl-methoxyacetamide) xHCl |
| VII(12) | (4-chloro-6-methoxyquinazolinyl-oxy-cyclohexyl-N-methyl-N',N'-dimethylurea) xHCl |
| VII(13) | (4-chloro-6-methoxyquinazolinyl-oxy-cyclohexyl-N-methyl-acetamide) xHCl |
| VII(14) | (4-chloro-6-methoxyquinazolinyl-oxy-cyclohexyl-N-methyl-methoxyacetamide) xHCl |
| VII(15) | (4-chloro-6-methoxyquinazolinyl-oxy-cyclohexyl-N-methyl-N',N'-dimethylurea) xHCl |

The free bases of the above-mentioned compounds may also be obtained by alkaline working up.

Example VIII

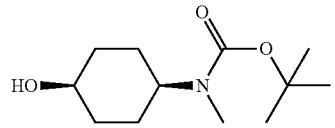 [SMILES: CN(C(=O)OC(C)(C)C)[C@H]1CC[C@@H](O)CC1]

cis-1-Hydroxy-4-(N-tert-butyloxycarbonyl-N-methyl-amino)-cyclohexane

Prepared by reacting cis-1-hydroxy-4-methylamino-cyclohexane with di-tert-butyl pyrocarbonate in ethyl acetate at ambient temperature.

Mass spectrum (ESI$^+$): m/z=230 [M+H]$^+$

The following may be obtained analogously to Example VIII:

| Example | Structure |
|---|---|
| VIII(1) | (cis-1-hydroxy-4-(N-ethoxycarbonyl-N-methyl-amino)-cyclohexane) |
| VIII(2) | (cis-1-hydroxy-4-(N-methoxycarbonyl-N-methyl-amino)-cyclohexane) |

-continued

| Example | Structure |
|---|---|
| VIII(3) | 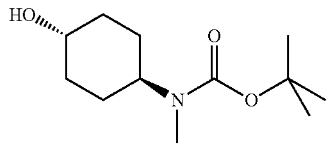 [SMILES: CN(C(=O)OC(C)(C)C)[C@H]1CC[C@H](O)CC1] |
| VIII(4) | 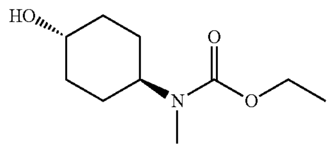 |
| VIII(5) | 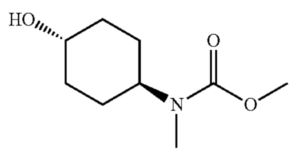 |
| VIII(6) | 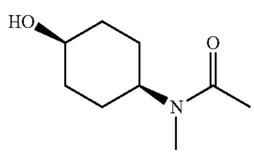 |
| VIII(7) | 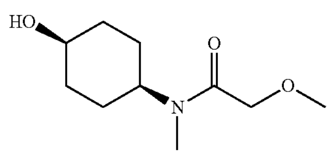 |
| VIII(8) | 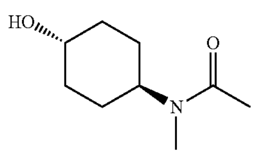 |
| VIII(9) | 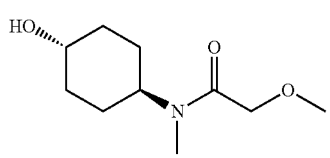 |

Example IX

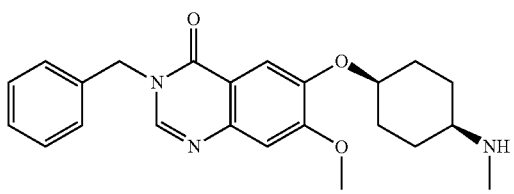 [SMILES: CN[C@H]1CC[C@@H](Oc2cc3c(=O)n(Cc4ccccc4)cnc3cc2OC)CC1]

3-Benzyl-3,4-dihydro-4-oxo-6-(cis-4-methylamino-cyclohexan-1-yloxy)-7-methoxy-quinazoline-hydrochloride Prepared by treating 3-benzyl-3,4-dihydro-4-oxo-6-{cis-4-[N-(tert-butyloxycarbonyl)-N-methyl-amino]-cyclohexyl-oxy}-7-methoxy-quinazoline with isopropanolic hydrochloric acid in ethanol at 40° C.

Mass spectrum (ESI$^+$): m/z=394 [M+H]$^+$

The following may be obtained analogously to Example IX:

| Example | Structure |
|---|---|
| IX(1) | 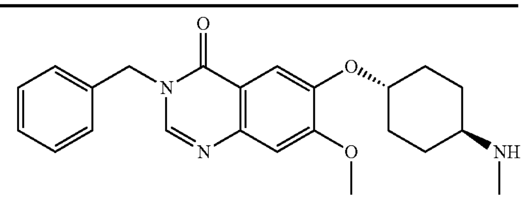 |
| IX(2) | 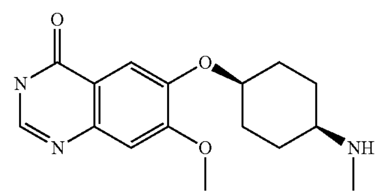 [SMILES: CN[C@H]1CC[C@@H](Oc2cc3c(=O)[nH]cnc3cc2OC)CC1] |
| IX(3) | 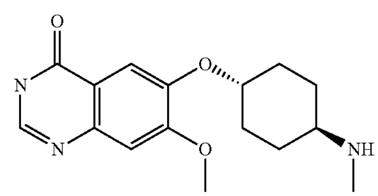 [SMILES: CN[C@H]1CC[C@H](Oc2cc3c(=O)[nH]cnc3cc2OC)CC1] |

Example X

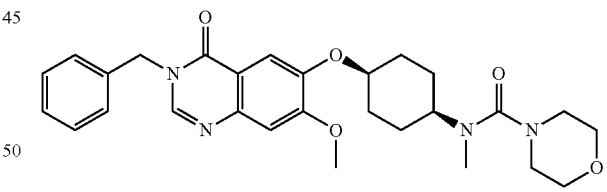

3-Benzyl-3,4-dihydro-4-oxo-6-[cis-4-(N-morpholinocarbonyl-N-methyl-amino)-cyclohexyl-oxy]-7-methoxy-quinazoline 1.18 ml morpholinocarbonyl chloride dissolved in 5 ml acetonitrile are added dropwise to a mixture of 3 g of 3-benzyl-3,4-dihydro-4-oxo-6-(cis-4-methylamino-cyclohexyl-oxy)-7-methoxy-quinazoline-hydrochloride, 2.67 ml of N-ethyl-diisopropylamine and 25 ml of acetonitrile, while cooling with an ice bath. After stirring overnight at ambient temperature the reaction mixture is divided between 50 ml of water and 30 ml of ethyl acetate. The aqueous phase is extracted with 50 ml of ethyl acetate and the combined organic phases are washed with 20 ml of water and saturated saline solution, dried and evaporated down. The residue is purified by chromatography through a silica gel column with methylene chloride/methanol (97:3 to 95:5).

Yield: 1.5 g (42% of theory)

$R_f$ value: 0.60 (silica gel; methylene chloride/methanol=9:1)

Mass spectrum (ESI$^+$): m/z=507 [M+H]$^+$

The following may be obtained analogously to Example X:

| Example | Structure |
|---|---|
| X(1) | 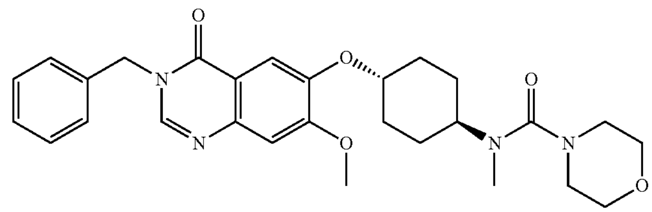 [SMILES: COc1cc2ncn(Cc3ccccc3)c(=O)c2cc1O[C@H]1CC[C@H](N(C)C(=O)N2CCOCC2)CC1] |
| X(2) | 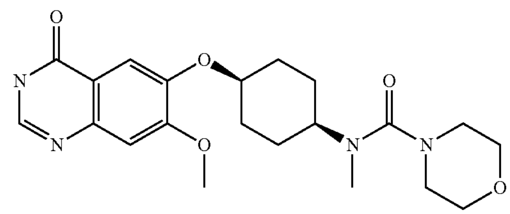 [SMILES: COc1cc2nc[nH]c(=O)c2cc1O[C@H]1CC[C@@H](N(C)C(=O)N2CCOCC2)CC1] |
| X(3) | 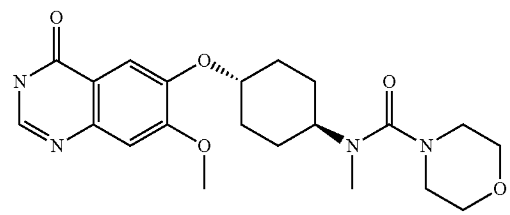 [SMILES: COc1cc2nc[nH]c(=O)c2cc1O[C@H]1CC[C@H](N(C)C(=O)N2CCOCC2)CC1] |
| X(4) | 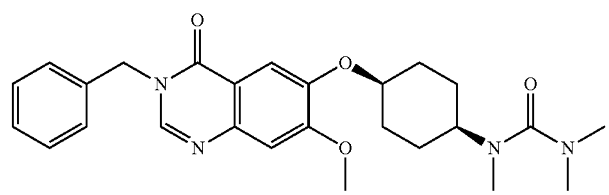 [SMILES: COc1cc2ncn(Cc3ccccc3)c(=O)c2cc1O[C@H]1CC[C@@H](N(C)C(=O)N(C)C)CC1] |
| X(5) | 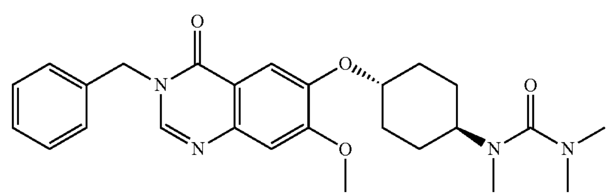 |
| X(6) | 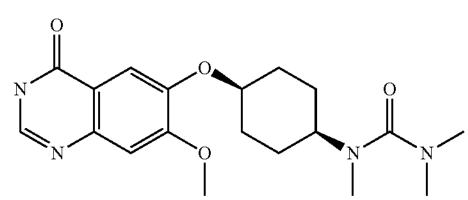 [SMILES: COc1cc2nc[nH]c(=O)c2cc1O[C@H]1CC[C@@H](N(C)C(=O)N(C)C)CC1] |
| X(7) | 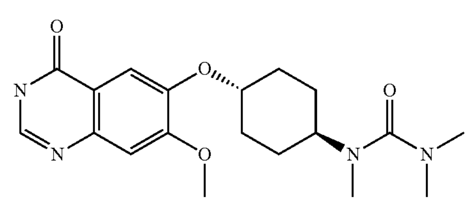 [SMILES: COc1cc2nc[nH]c(=O)c2cc1O[C@H]1CC[C@H](N(C)C(=O)N(C)C)CC1] |

-continued

| Example | Structure |
|---|---|
| X(8) | (structure) |
| X(9) | (structure) |
| X(10) | (structure) |
| X(11) | (structure) |
| X(12) | (structure) |
| X(13) | (structure) |
| X(14) | (structure) |
| X(15) | (structure) |

Preparation of the End Compounds
Example 1

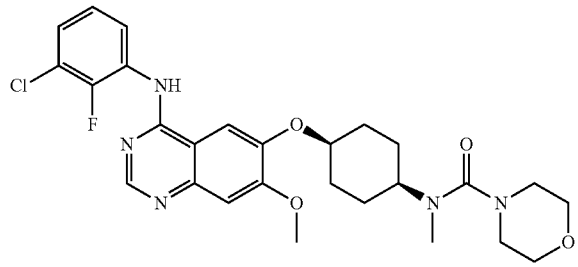 [SMILES: COc1cc2ncnc(Nc3cccc(Cl)c3F)c2cc1O[C@H]1CC[C@@H](N(C)C(=O)N2CCOCC2)CC1]

4-[(3-Chloro-2-fluoro-phenyl)amino]-6-[cis-4-(N-morpholinocarbonyl-N-methyl-amino)-cyclohexyl-oxy]-7-methoxy-quinazoline 800 mg of 3,4-dihydro-4-oxo-6-[cis-4-(N-morpholinocarbonyl-N-methyl-amino)-cyclohexyl-oxy]-7-methoxy-quinazoline, 7 ml of thionyl chloride and 0.1 ml dimethylformamide are refluxed for 3 hours. The volatile components of the reaction mixture are eliminated using the rotary evaporator, the residue is combined with toluene and concentrated again by rotary evaporation. The residue is combined with 30 ml isopropanol and 643 mg 3-chloro-2-fluoro-aniline. The mixture is refluxed for 1.5 hours. Then it is evaporated to dryness and the residue is divided between 70 ml of ethyl acetate and 30 ml 10% aqueous potassium carbonate solution. The organic phase is washed with water and saline solution, dried and evaporated down. The residue is purified by chromatography through a silica gel column with methylene chloride/methanol (95:5 to 70:30).

Yield: 580 mg (56% of theory)

$R_f$ value: 0.55 (silica gel; methylene chloride/methanol=7:1)

Mass spectrum (ESI$^+$): m/z=544, 546 [M+H]$^+$

The following may be obtained analogously to Example 1:

| Example 1 | Structure |
|---|---|
| (1) | (structure shown) Mass spectrum (ESI$^+$): m/z = 544, 546 [M + H]$^+$ |
| (2) | (structure shown) |
| (3) | (structure shown) |
| (4) | (structure shown) |

-continued
| Example 1 | Structure |
|---|---|
| (5) | 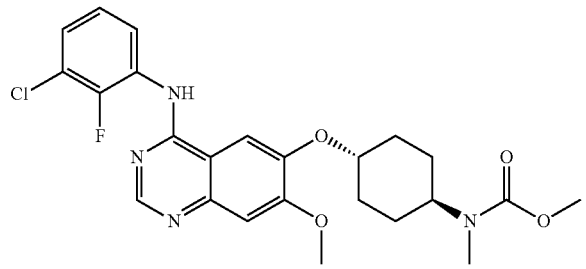 [SMILES: COC(=O)N(C)[C@H]1CC[C@H](Oc2cc3c(Nc4cccc(Cl)c4F)ncnc3cc2OC)CC1] |
| (6) | 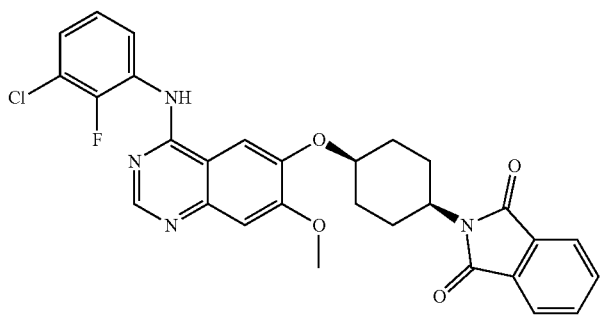 [SMILES: COc1cc2ncnc(Nc3cccc(Cl)c3F)c2cc1O[C@H]1CC[C@@H](N2C(=O)c3ccccc3C2=O)CC1] |
| (7) | 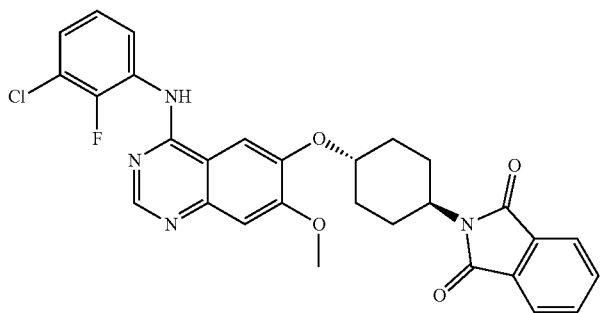 [SMILES: COc1cc2ncnc(Nc3cccc(Cl)c3F)c2cc1O[C@H]1CC[C@H](N2C(=O)c3ccccc3C2=O)CC1] |
| (8) | 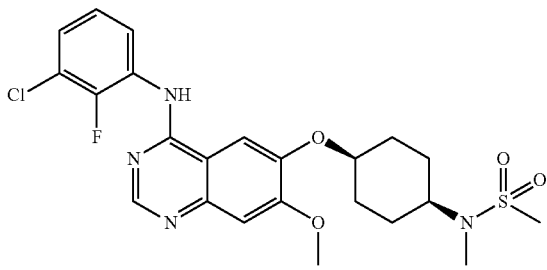 |
| (9) | 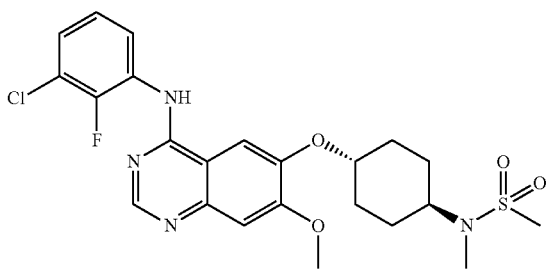 [SMILES: COc1cc2ncnc(Nc3cccc(Cl)c3F)c2cc1O[C@H]1CC[C@H](N(C)S(C)(=O)=O)CC1] |

-continued
| Example 1 | Structure |
|---|---|
| (10) | 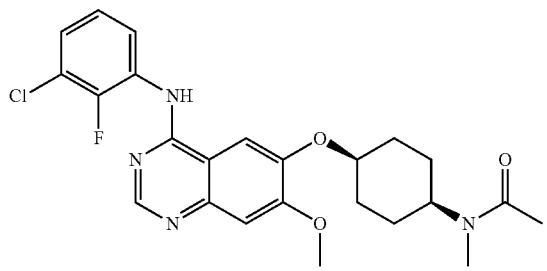 [SMILES: COc1cc2ncnc(Nc3cccc(Cl)c3F)c2cc1O[C@H]1CC[C@@H](N(C)C(C)=O)CC1] |
| (11) | 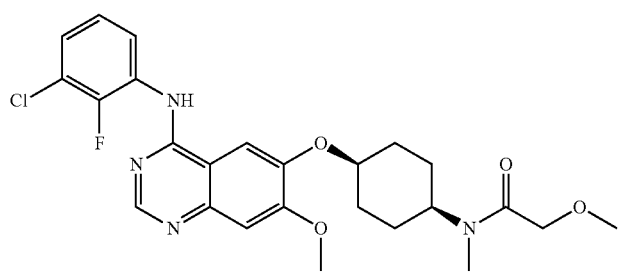 [SMILES: COCC(=O)N(C)[C@H]1CC[C@@H](Oc2cc3c(Nc4cccc(Cl)c4F)ncnc3cc2OC)CC1] |
| (12) | 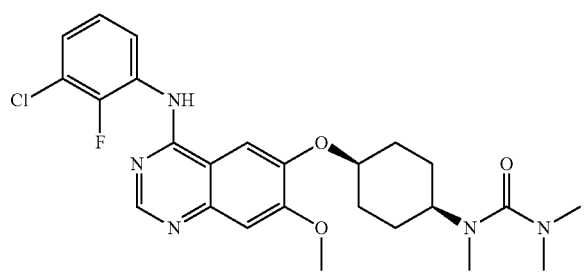 [SMILES: COc1cc2ncnc(Nc3cccc(Cl)c3F)c2cc1O[C@H]1CC[C@@H](N(C)C(=O)N(C)C)CC1] |
| (13) | 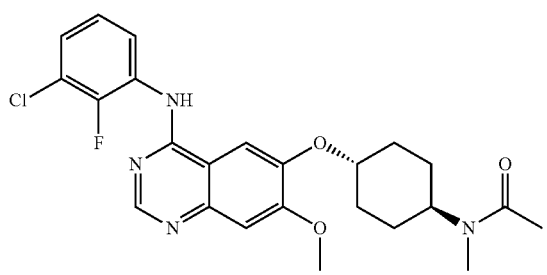 [SMILES: COc1cc2ncnc(Nc3cccc(Cl)c3F)c2cc1O[C@H]1CC[C@H](N(C)C(C)=O)CC1] |
| (14) | 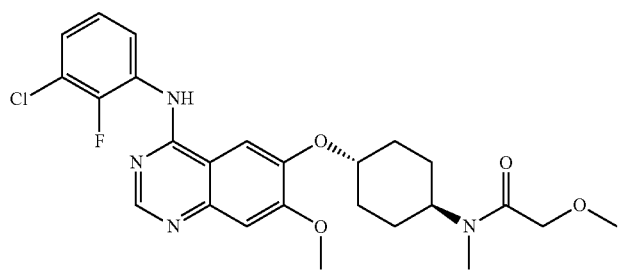 |

| Example 1 | Structure |
|---|---|
| (15) | 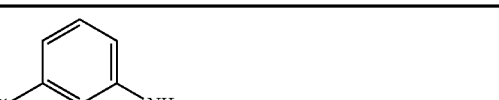 |
The following compounds may also be prepared analogously to the above-mentioned Examples and other methods known from the literature:
| Example 1 | Structure |
|---|---|
| (16) | 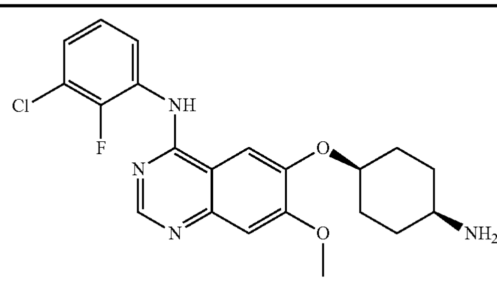 |
| (17) | 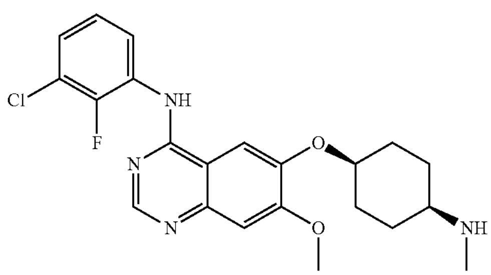 [SMILES: CN[C@H]1CC[C@@H](Oc2cc3c(Nc4cccc(Cl)c4F)ncnc3cc2OC)CC1] |
| (18) | 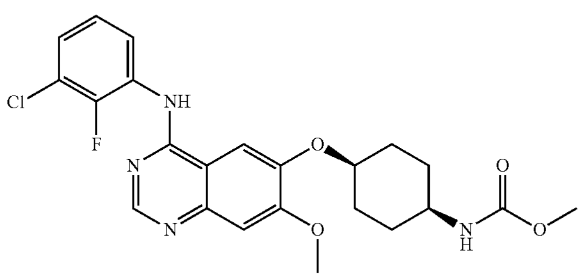 [SMILES: COC(=O)N[C@H]1CC[C@@H](Oc2cc3c(Nc4cccc(Cl)c4F)ncnc3cc2OC)CC1] |
| (19) | 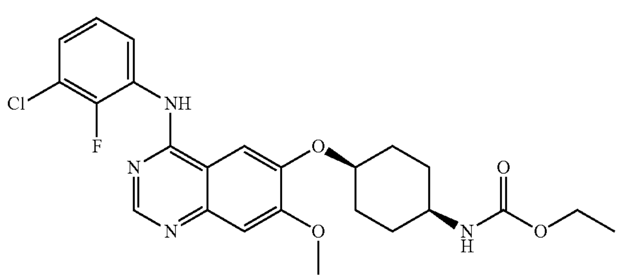 [SMILES: CCOC(=O)N[C@H]1CC[C@@H](Oc2cc3c(Nc4cccc(Cl)c4F)ncnc3cc2OC)CC1] |

| Example 1 | Structure |
|---|---|
| (20) | 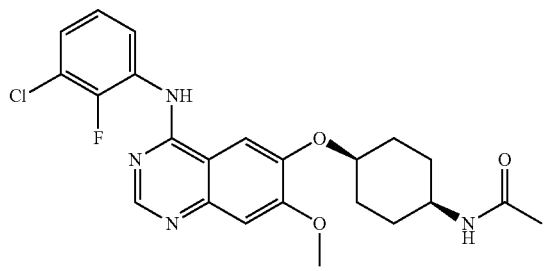 [SMILES: COc1cc2ncnc(Nc3cccc(Cl)c3F)c2cc1O[C@H]1CC[C@@H](NC(C)=O)CC1] |
| (21) | 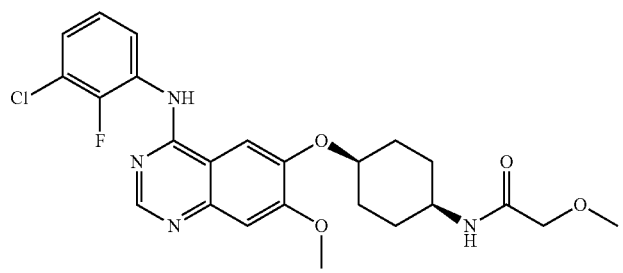 [SMILES: COCC(=O)N[C@H]1CC[C@@H](Oc2cc3c(Nc4cccc(Cl)c4F)ncnc3cc2OC)CC1] |
| (22) | 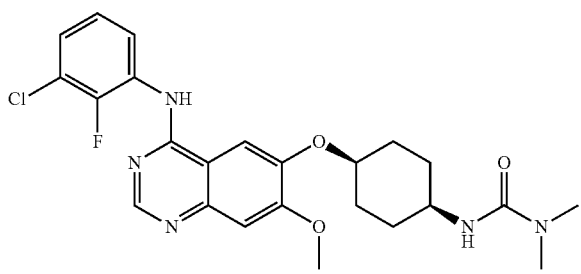 [SMILES: COc1cc2ncnc(Nc3cccc(Cl)c3F)c2cc1O[C@H]1CC[C@@H](NC(=O)N(C)C)CC1] |
| (23) | 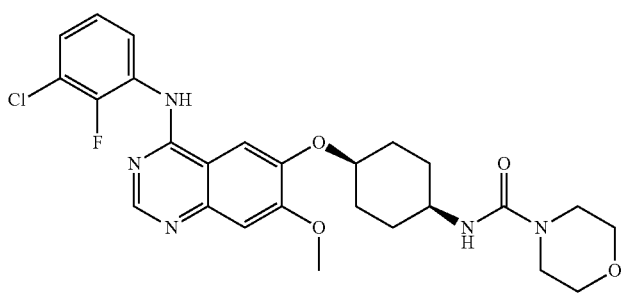
Mass spectrum (ESI⁺): m/z = 530, 532 [M + H]⁺ |
| (24) | 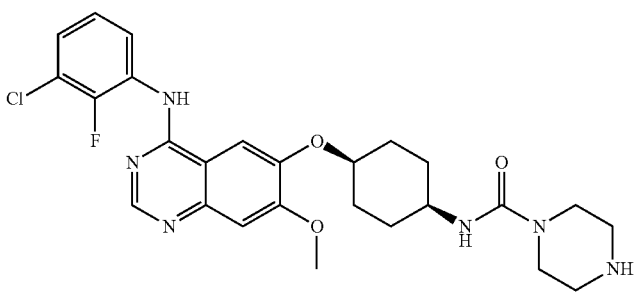 [SMILES: COc1cc2ncnc(Nc3cccc(Cl)c3F)c2cc1O[C@H]1CC[C@@H](NC(=O)N2CCNCC2)CC1] |

| Example 1 | Structure |
|---|---|
| (25) | 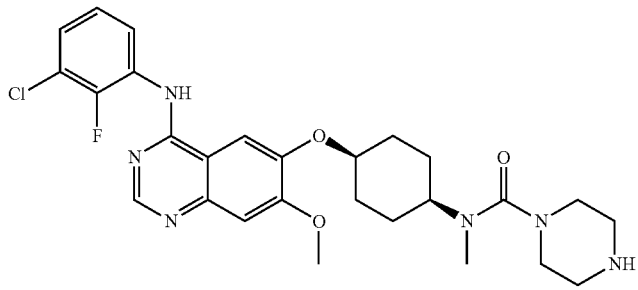 [SMILES: COc1cc2ncnc(Nc3cccc(Cl)c3F)c2cc1O[C@H]1CC[C@@H](N(C)C(=O)N2CCNCC2)CC1] |
| (26) | 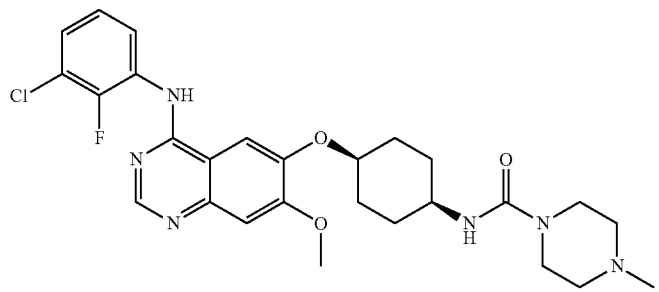 [SMILES: COc1cc2ncnc(Nc3cccc(Cl)c3F)c2cc1O[C@H]1CC[C@@H](NC(=O)N2CCN(C)CC2)CC1] |
| (27) | 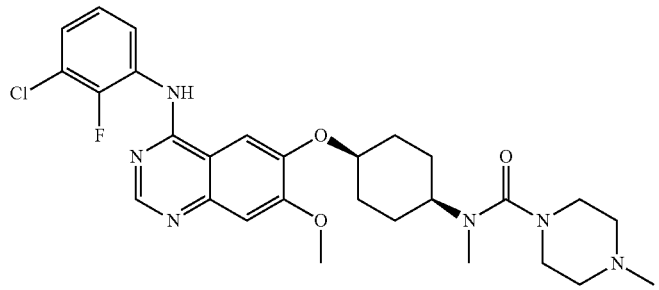 [SMILES: COc1cc2ncnc(Nc3cccc(Cl)c3F)c2cc1O[C@H]1CC[C@@H](N(C)C(=O)N2CCN(C)CC2)CC1] |
| (28) | 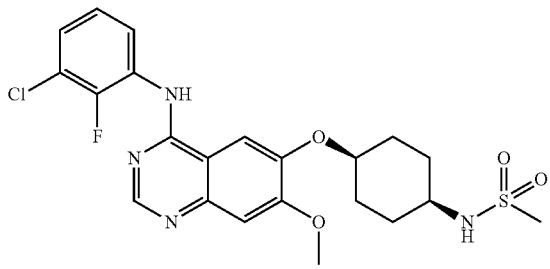 [SMILES: COc1cc2ncnc(Nc3cccc(Cl)c3F)c2cc1O[C@H]1CC[C@@H](NS(C)(=O)=O)CC1] |
| (29) | 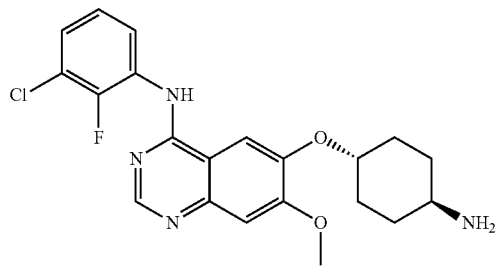 [SMILES: COc1cc2ncnc(Nc3cccc(Cl)c3F)c2cc1O[C@H]1CC[C@H](N)CC1] |

-continued
| Example 1 | Structure |
|---|---|
| (30) | 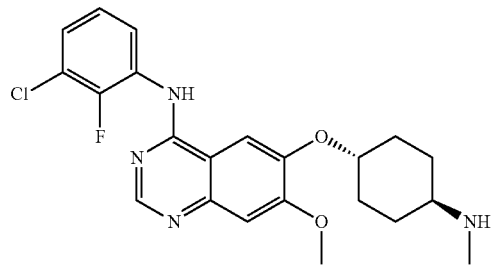 [SMILES: CN[C@H]1CC[C@H](Oc2cc3c(Nc4cccc(Cl)c4F)ncnc3cc2OC)CC1] |
| (31) | 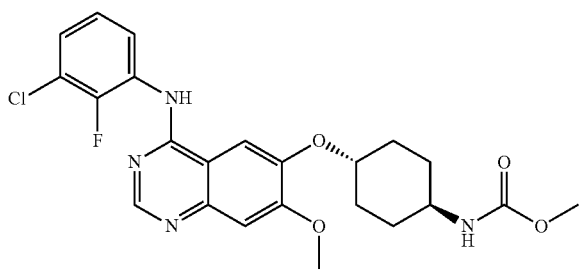 [SMILES: COC(=O)N[C@H]1CC[C@H](Oc2cc3c(Nc4cccc(Cl)c4F)ncnc3cc2OC)CC1] |
| (32) | 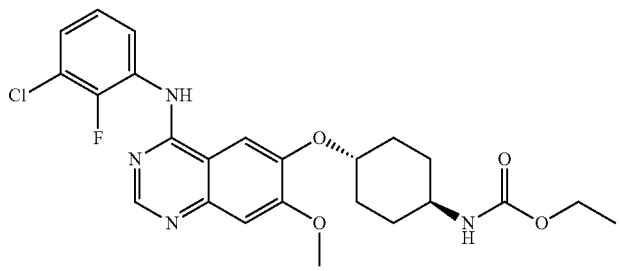 [SMILES: CCOC(=O)N[C@H]1CC[C@H](Oc2cc3c(Nc4cccc(Cl)c4F)ncnc3cc2OC)CC1] |
| (33) | 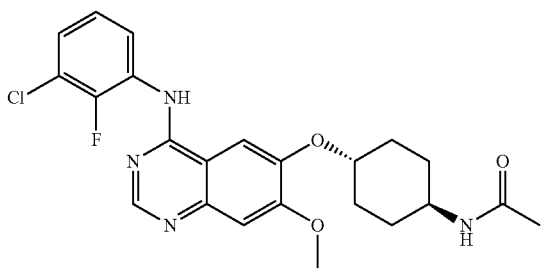 [SMILES: COc1cc2ncnc(Nc3cccc(Cl)c3F)c2cc1O[C@H]1CC[C@H](NC(C)=O)CC1] |
| (34) | 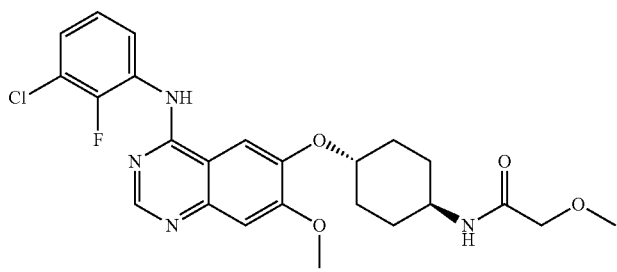 [SMILES: COCC(=O)N[C@H]1CC[C@H](Oc2cc3c(Nc4cccc(Cl)c4F)ncnc3cc2OC)CC1] |

| Example 1 | Structure |
|---|---|
| (35) | 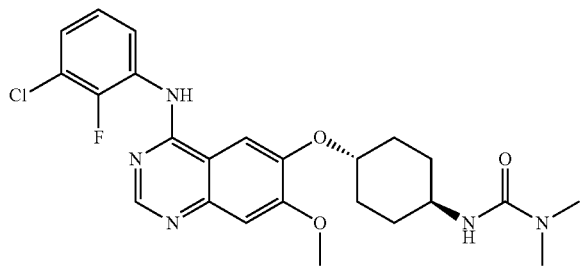 [SMILES: COc1cc2ncnc(Nc3cccc(Cl)c3F)c2cc1O[C@H]1CC[C@H](NC(=O)N(C)C)CC1] |
| (36) | 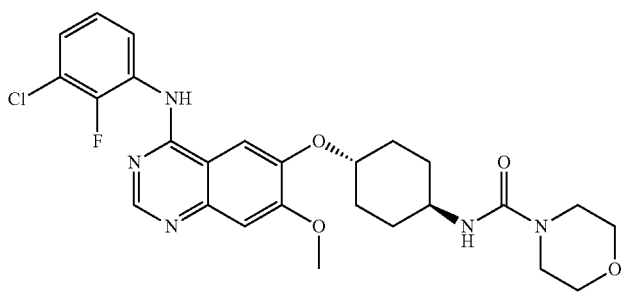
Mass spectrum (ESI+): m/z = 530, 532 [M + H]+ |
| (37) | 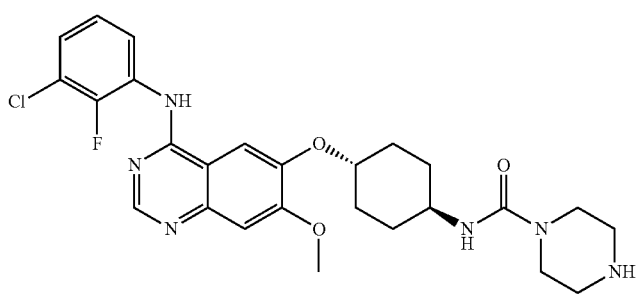 [SMILES: COc1cc2ncnc(Nc3cccc(Cl)c3F)c2cc1O[C@H]1CC[C@H](NC(=O)N2CCNCC2)CC1] |
| (38) | 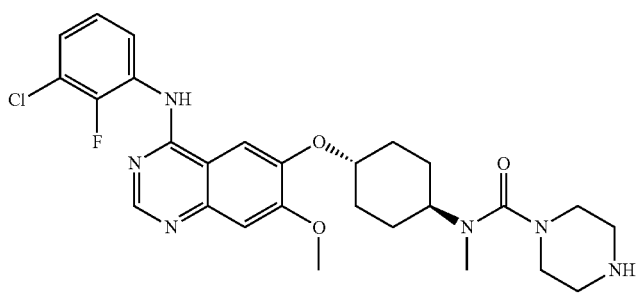 [SMILES: COc1cc2ncnc(Nc3cccc(Cl)c3F)c2cc1O[C@H]1CC[C@H](N(C)C(=O)N2CCNCC2)CC1] |
| (39) | 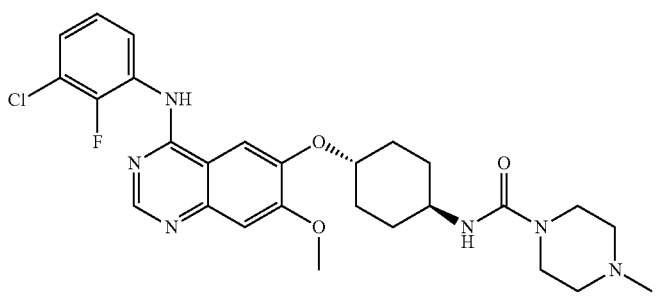 [SMILES: COc1cc2ncnc(Nc3cccc(Cl)c3F)c2cc1O[C@H]1CC[C@H](NC(=O)N2CCN(C)CC2)CC1] |

| Example 1 | Structure |
|---|---|
| (40) | 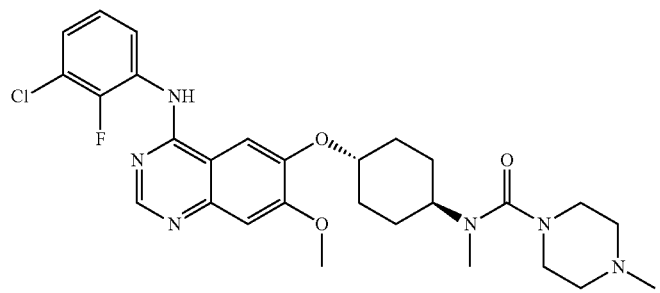 [SMILES: COc1cc2ncnc(Nc3cccc(Cl)c3F)c2cc1O[C@H]1CC[C@H](N(C)C(=O)N2CCN(C)CC2)CC1] |
| (41) | 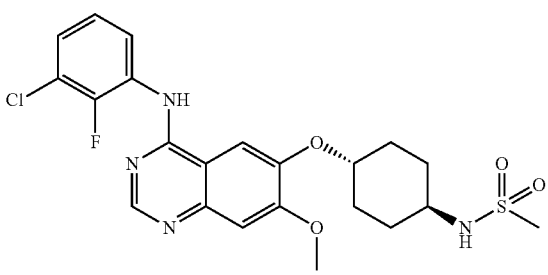 [SMILES: COc1cc2ncnc(Nc3cccc(Cl)c3F)c2cc1O[C@H]1CC[C@H](NS(C)(=O)=O)CC1] |

Example 2

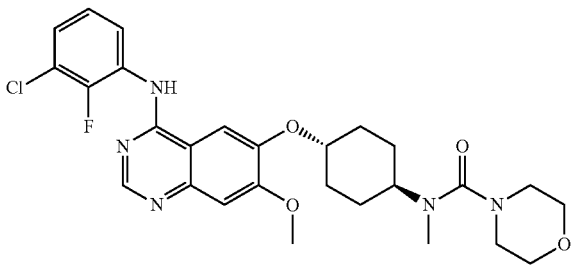 [SMILES: COc1cc2ncnc(Nc3cccc(Cl)c3F)c2cc1O[C@H]1CC[C@H](N(C)C(=O)N2CCOCC2)CC1]

4-[(3-Chloro-2-fluoro-phenyl)amino]-6-[trans-4-(N-morpholinocarbonyl-N-methyl-amino)-cyclohexyl-oxy]-7-methoxy-quinazoline 2600 mg 4-[(3-chloro-2-fluoro-phenyl)amino]-6-[trans-4-(methylamino)-cyclohexyl-oxy]-7-methoxy-quinazoline-hydrochloride are suspended in 20 ml acetonitrile, then 3.1 ml triethylamine are added and 0.723 ml morpholine-N-carbonyl chloride, dissolved in 5 ml acetonitrile, are added dropwise at <8° C. After stirring overnight at ambient temperature the reaction mixture is diluted with ethyl acetate and the organic phase is extracted with water and saline solution. The organic phase is dried and evaporated down. The residue is stirred out with acetonitrile, the solid is suction filtered and dried.

Mass spectrum (ESI$^+$): m/z=544, 546 [M+H]$^+$

The following may be obtained analogously to Example 2:

| Example 2 | Structure |
|---|---|
| (1) | 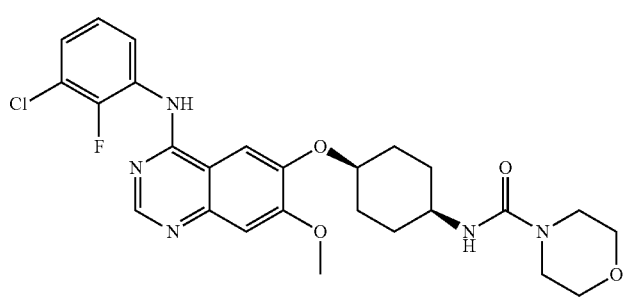 |

Mass spectrum (ESI$^+$): m/z = 530, 532 [M + H]$^+$

| Example 2 | Structure |
|---|---|
| (2) | 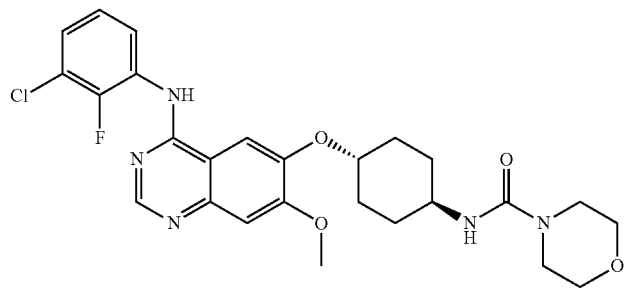
Mass spectrum (ESI⁺): m/z = 530, 532 [M + H]⁺ |

Example 3

4-[(3-chloro-2-fluoro-phenyl)amino]-6-[cis-4-(tert.-butoxycarbonyl-amino)-cyclohexyl-oxy]-7-methoxy-quinazoline Prepared by reacting 5 g of 4-[(3-chloro-2-fluoro-phenyl)amino]-6-hydroxy-7-methoxy-quinazoline and 8.7 g of the compound of Example IV (16) in the presence of 4.3 g potassium carbonate in 40 ml N,N-dimethylformamide at 80° C.

Mass spectrum (ESI⁺): m/z=517, 519 [M+H]⁺

The following may be obtained analogously to Example 3:

| Example 3 | Structure |
|---|---|
| (1) | 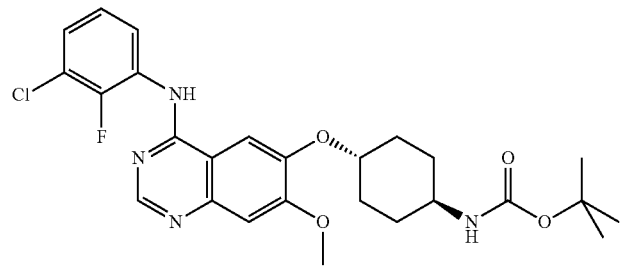
Mass spectrum (ESI⁺): m/z = 517, 519 [M + H]⁺ |
| (2) | 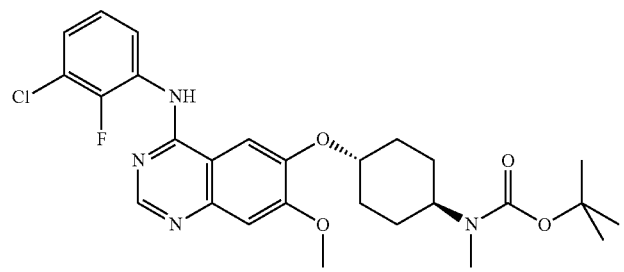
Mass spectrum (ESI⁺): m/z = 531, 533 [M + H]⁺ |

| Example 3 | Structure |
|---|---|
| (3) | 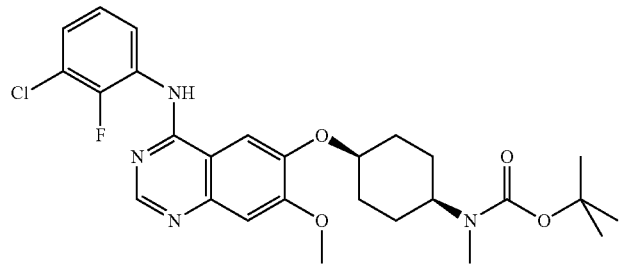<br>Mass spectrum (ESI$^+$): m/z = 531, 533 [M + H]$^+$ |

Example 4

4-[(3-Chloro-2-fluoro-phenyl)amino]-6-[cis-4-(amino)-cyclohexyl-oxy]-7-methoxy-quinazoline-dihydrochloride Prepared by treating 843 mg of the compound of Example 3 with 3.3 ml isopropanolic hydrochloric acid (5-6 M) in 8 ml dichloromethane at ambient temperature.

Mass spectrum (ESI$^+$): m/z=417, 419 [M+H]$^+$

The following compounds are obtained analogously to Example 4:

| Example 4 | Structure |
|---|---|
| (1) | 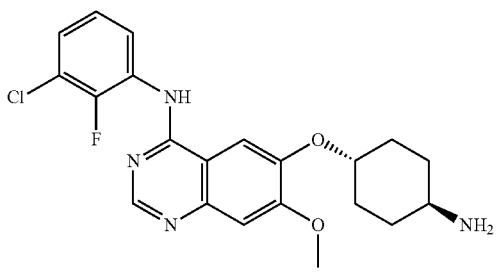<br>Mass spectrum (ESI$^+$): m/z = 417, 419 [M + H]$^+$ |
| (2) | 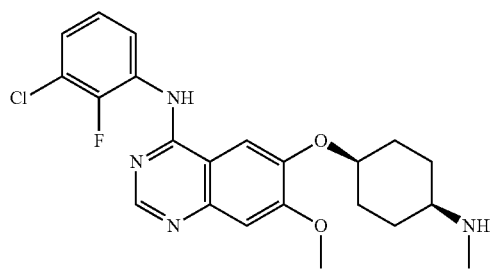<br>Mass spectrum (ESI$^+$): m/z = 431, 433 [M + H]$^+$ |
| (3) | 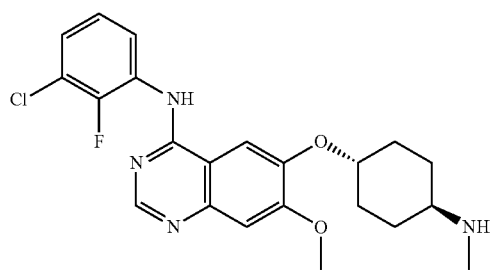<br>Mass spectrum (ESI$^+$): m/z = 431, 433 [M + H]$^+$ |

Example 5

Coated tablets containing 75 mg of active substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl-pyrrolidone, hydroxypropylmethyl-cellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| die: | 9 mm, convex |

The tablet cores thus produced are coated with a film consisting essentially of hydroxypropylmethylcellulose. The finished film-coated tablets are polished with beeswax.
Weight of coated tablet: 245 mg.

Example 6

Tablets containing 100 mg of active substance
Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

Example 7

Tablets containing 150 mg of active substance
Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

Example 8

Hard gelatine capsules containing 150 mg of active substance

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

Example 9

Suppositories containing 150 mg of active substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

Example 10

Suspension containing 50 mg of active substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |

-continued

| 100 ml of suspension contain: | |
|---|---|
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 11

Ampoules containing 10 mg active substance
Composition:

| active substance | 10.0 mg |
|---|---|
| 0.01N hydrochloric acid | q.s. |
| double-distilled water | ad 2.0 ml |

Preparation:

The active substance is dissolved in the requisite amount of 0.01 N HCl, made isotonic with common salt, filtered sterile and transferred into 2 ml ampoules.

Example 12

Ampoules containing 50 mg of active substance
Composition:

| active substance | 50.0 mg |
|---|---|
| 0.01N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

Example 13

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule | 3 |

Example 14

Solution for inhalation for hand-held nebulisers containing 2.5 mg active substance

| 1 spray contains: | |
|---|---|
| active substance | 2.500 mg |
| benzalkonium chloride | 0.001 mg |
| 1N hydrochloric acid | q.s. |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

The invention claimed is:
1. A bicyclic heterocycle of formula (I)

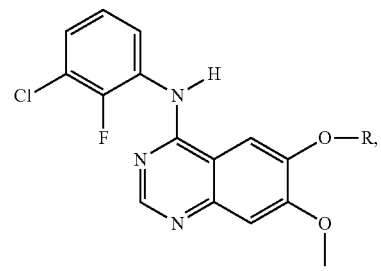

wherein
R denotes a group selected from among
cis-4-amino-cyclohexyl, trans-4-amino-cyclohexyl,
cis-4-methylamino-cyclohexyl, trans-4-methylamino-cyclohexyl,
cis-4-(methoxycarbonylamino)-cyclohexyl, trans-4-(methoxycarbonylamino)-cyclohexyl,
cis-4-(N-methoxycarbonyl-N-methyl-amino)-cyclohexyl, trans-4-(N-methoxycarbonyl-N-methyl-amino)-cyclohexyl,
cis-4-(ethyloxycarbonylamino)-cyclohexyl, trans-4-(ethyloxycarbonylamino)-cyclohexyl,
cis-4-(N-ethyloxycarbonyl-N-methyl-amino)-cyclohexyl, trans-4-(N-ethyloxycarbonyl-N-methyl-amino)-cyclohexyl,
cis-4-(tert.-butoxycarbonylamino)-cyclohexyl, trans-4-(tert.-butoxycarbonylamino)-cyclohexyl,
cis-4-(N-tert.-butoxycarbonyl-N-methyl-amino)-cyclohexyl, trans-4-(N-tert.-butoxycarbonyl-N-methyl-amino)-cyclohexyl,
cis-4-(acetylamino)-cyclohexyl, trans-4-(acetylamino)-cyclohexyl,
cis-4-(N-acetyl-N-methyl-amino)-cyclohexyl, trans-4-(N-acetyl-N-methyl-amino)-cyclohexyl, cis-4-(methoxyacetyl-amino)-cyclohexyl, trans-4-(methoxyacetyl-amino)-cyclohexyl,
cis-4-(N-methoxyacetyl-N-methyl-amino)-cyclohexyl, trans-4-(N-methoxyacetyl-N-methyl-amino)-cyclohexyl,
cis-4-(dimethylaminocarbonyl-amino)-cyclohexyl, trans-4-(dimethylaminocarbonyl-amino)-cyclohexyl,
cis-4-(N-dimethylaminocarbonyl-N-methyl-amino)-cyclohexyl, trans-4-(N-dimethylaminocarbonyl-N-methyl-amino)-cyclohexyl,
cis-4-(morpholinocarbonyl-amino)-cyclohexyl, trans-4-(morpholinocarbonyl-amino)-cyclohexyl,
cis-4-(N-morpholinocarbonyl-N-methyl-amino)-cyclohexyl, trans-4-(N-morpholinocarbonyl-N-methyl-amino)-cyclohexyl,
cis-4-(piperazin-1-ylcarbonyl-amino)-cyclohexyl, trans-4-(piperazin-1-ylcarbonyl-amino)-cyclohexyl,
cis-4-(N-piperazin-1-ylcarbonyl-N-methyl-amino)-cyclohexyl, trans-4-(N-piperazin-1-ylcarbonyl-N-methyl-amino)-cyclohexyl,
cis-4-[(4-methyl-piperazin-1-ylcarbonyl)-amino]-cyclohexyl, trans-4-[(4-methyl-piperazin-1-ylcarbonyl)-amino]-cyclohexyl,
cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl,
cis-4-(methanesulphonylamino)-cyclohexyl, trans-4-(methanesulphonylamino)-cyclohexyl,
cis-4-(N-methanesulphonyl-N-methyl-amino)-cyclohexyl, trans-4-(N-methanesulphonyl-N-methyl-amino)-cyclohexyl, cis-4-phthalimido-cyclohexyl and trans-4-phthalimido-cyclohexyl,
or a tautomer or pharmacologically acceptable acid addition salt thereof.

2. The compound according to claim 1, wherein
R denotes a group selected from among
cis-4-(methoxycarbonylamino)-cyclohexyl, trans-4-(methoxycarbonylamino)-cyclohexyl,
cis-4-(N-methoxycarbonyl-N-methyl-amino)-cyclohexyl, trans-4-(N-methoxycarbonyl-N-methyl-amino)-cyclohexyl,
cis-4-(ethyloxycarbonylamino)-cyclohexyl, trans-4-(ethyloxycarbonylamino)-cyclohexyl,
cis-4-(N-ethyloxycarbonyl-N-methyl-amino)-cyclohexyl, trans-4-(N-ethyloxycarbonyl-N-methyl-amino)-cyclohexyl,
cis-4-(tert.-butoxycarbonylamino)-cyclohexyl, trans-4-(tert.-butoxycarbonylamino)-cyclohexyl,
cis-4-(N-tert.-butoxycarbonyl-N-methyl-amino)-cyclohexyl, trans-4-(N-tert.-butoxycarbonyl-N-methyl-amino)-cyclohexyl,
cis-4-(methoxyacetyl-amino)-cyclohexyl, trans-4-(methoxyacetyl-amino)-cyclohexyl,
cis-4-(N-methoxyacetyl-N-methyl-amino)-cyclohexyl, trans-4-(N-methoxyacetyl-N-methyl-amino)-cyclohexyl,
cis-4-(dimethylaminocarbonyl-amino)-cyclohexyl, trans-4-(dimethylaminocarbonyl-amino)-cyclohexyl,
cis-4-(N-dimethylaminocarbonyl-N-methyl-amino)-cyclohexyl, trans-4-(N-dimethylaminocarbonyl-N-methyl-amino)-cyclohexyl,
cis-4-(morpholinocarbonyl-amino)-cyclohexyl, trans-4-(morpholinocarbonyl-amino)-cyclohexyl,
cis-4-(N-morpholinocarbonyl-N-methyl-amino)-cyclohexyl, trans-4-(N-morpholinocarbonyl-N-methyl-amino)-cyclohexyl,
cis-4-(piperazin-1-ylcarbonyl-amino)-cyclohexyl, trans-4-(piperazin-1-ylcarbonyl-amino)-cyclohexyl,
cis-4-(N-piperazin-1-ylcarbonyl-N-methyl-amino)-cyclohexyl, trans-4-(N-piperazin-1-ylcarbonyl-N-methyl-amino)-cyclohexyl,
cis-4-[(4-methyl-piperazin-1-ylcarbonyl)-amino]-cyclohexyl, trans-4-[(4-methyl-piperazin-1-ylcarbonyl)-amino]-cyclohexyl,
cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl,
cis-4-(methanesulphonylamino)-cyclohexyl, trans-4-(methanesulphonylamino)-cyclohexyl,
cis-4-(N-methanesulphonyl-N-methyl-amino)-cyclohexyl, trans-4-(N-methanesulphonyl-N-methyl-amino)-cyclohexyl, cis-4-phthalimido-cyclohexyl and trans-4-phthalimido-cyclohexyl,
or a tautomer or pharmacologically acceptable acid addition salt thereof.

3. A physiologically acceptable salt of the compound according to claim 1 with an inorganic or organic acid.

4. A pharmaceutical composition containing a compound according to claim 1 or a pharmacologically acceptable acid addition salt thereof, optionally together with one or more inert carriers and/or diluents.

5. A process for preparing the compound of formula I according to claim 1, comprising
a) reacting a compound of formula (II)

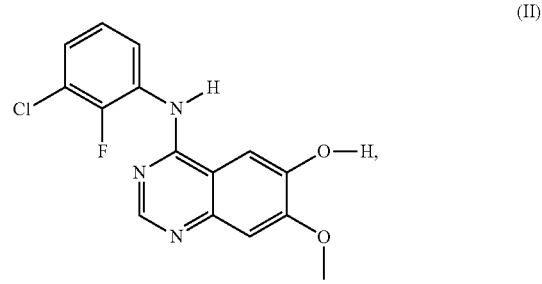

(II)

with a compound of general formula (III)

$Z^1$—R    (III), wherein,
R is defined as in claim 1, and
$Z^1$ denotes a leaving group or hydroxy group, or
b) reacting a compound of general formula (IV)

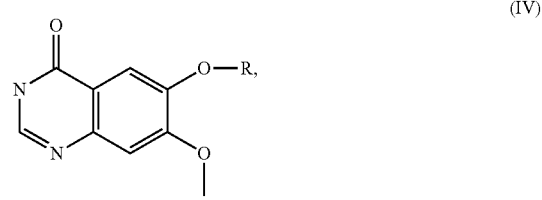

(IV)

wherein R is defined as in claim 1,
with a halogenating agent to form an intermediate compound of general formula (V),

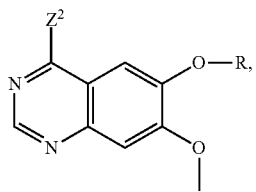

(V)

wherein R is defined as in claim 1, and $Z^2$ denotes a halogen atom, and then reacting (V) with 3-chloro-2-fluoro-aniline.

6. A process for preparing the compound of formula (I) according to claim 1, wherein R denotes a group selected from among cis-4-(methoxycarbonylamino)-cyclohexyl, trans-4-(methoxycarbonylamino)-cyclohexyl, cis-4-(N-methoxycarbonyl-N-methyl-amino)-cyclohexyl, trans-4-(N-methoxycarbonyl-N-methyl-amino)-cyclohexyl, cis-4-(ethyloxycarbonylamino)-cyclohexyl, trans-4-(ethyloxycarbonylamino)-cyclohexyl, cis-4-(N-ethyloxycarbonyl-N-methyl-amino)-cyclohexyl, trans-4-(N-ethyloxycarbonyl-N-methyl-amino)-cyclohexyl, cis-4-(tert.-butoxycarbonylamino)-cyclohexyl, trans-4-(tert.-butoxycarbonylamino)-cyclohexyl, cis-4-(N-tert.-butoxycarbonyl-N-methyl-amino)-cyclohexyl, trans-4-(N-tert.-butoxycarbonyl-N-methyl-amino)-cyclohexyl, cis-4-(acetylamino)-cyclohexyl, trans-4-(acetylamino)-cyclohexyl, cis-4-(N-acetyl-N-methyl-amino)-cyclohexyl, trans-4-(N-acetyl-N-methyl-amino)-cyclohexyl, cis-4-(methoxyacetyl-amino)-cyclohexyl, trans-4-(methoxyacetyl-amino)-cyclohexyl, cis-4-(N-methoxyacetyl-N-methyl-amino)-cyclohexyl, trans-4-(N-methoxyacetyl-N-methyl-amino)-cyclohexyl, cis-4-(dimethylaminocarbonyl-amino)-cyclohexyl, trans-4-(dimethylaminocarbonyl-amino)-cyclohexyl, cis-4-(N-dimethylaminocarbonyl-N-methyl-amino)-cyclohexyl, trans-4-(N-dimethylaminocarbonyl-N-methyl-amino)-cyclohexyl, cis-4-(morpholinocarbonyl-amino)-cyclohexyl, trans-4-(morpholinocarbonyl-amino)-cyclohexyl, cis-4-(N-morpholinocarbonyl-N-methyl-amino)-cyclohexyl, trans-4-(N-morpholinocarbonyl-N-methyl-amino)-cyclohexyl, cis-4-(piperazin-1-ylcarbonyl-amino)-cyclohexyl, trans-4-(piperazin-1-ylcarbonyl-amino)-cyclohexyl, cis-4-(N-piperazin-1-ylcarbonyl-N-methyl-amino)-cyclohexyl, trans-4-(N-piperazin-1-ylcarbonyl-N-methyl-amino)-cyclohexyl, cis-4-[(4-methyl-piperazin-1-ylcarbonyl)-amino]-cyclohexyl, trans-4-[(4-methyl-piperazin-1-ylcarbonyl)-amino]-cyclohexyl, cis-4-[N-(4-methyl-piperazin-1-ylcarbonyl)-N-methyl-amino]-cyclohexyl, trans-4-[N-(4-methyl-piperazin-1-ylcarbonyl)-N-methyl-amino]-cyclohexyl, cis-4-(methanesulphonylamino)-cyclohexyl, trans-4-(methanesulphonylamino)-cyclohexyl, cis-4-(N-methanesulphonyl-N-methyl-amino)-cyclohexyl and trans-4-(N-methanesulphonyl-N-methyl-amino)-cyclohexyl, comprising reacting a compound of formula (VI)

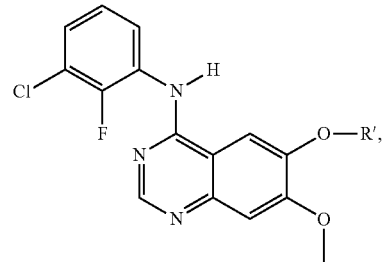

(VI)

wherein

R' denotes a group selected from among cis-4-amino-cyclohex-1-yl, trans-4-amino-cyclohex-1-yl, cis-4-(methylamino)-cyclohex-1-yl and trans-4-(methylamino)-cyclohex-1-yl, with a corresponding acylating agent.

7. A process for preparing the compound of formula (I) according to claim 1, wherein R denotes a cis-4-phthalimido-cyclohex-1-yl or trans-4-phthalimido-cyclohex-1-yl group, comprising reacting a compound of formula (VII)

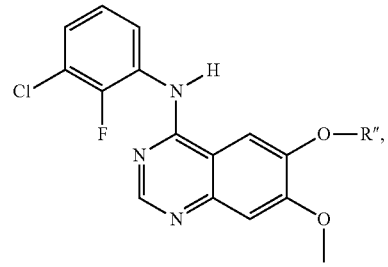

(VII)

wherein

R'' denotes a cis-4-amino-cyclohex-1-yl or trans-4-amino-cyclohex-1-yl group, with phthalic anhydride or another reactive derivative of phthalic acid.

8. A medicament combination which contains in addition to one or more compounds of formula I according to claim 1 or a pharmaceutically acceptable acid addition salt thereof and, as a further active substance, one or more compounds selected from among the categories of the betamimetics, anticholinergics, corticosteroids, other PDE4-inhibitors, LTD4-antagonists, EGFR-inhibitors, dopamine agonists, H1-antihistamines, PAF-antagonists, PI3-kinase inhibitors, MPR4-inhibitors, iNOS-inhibitors and SYK-inhibitors or double or triple combinations thereof.

\* \* \* \* \*

UNITED STATES PATENT AND TRADEMARK OFFICE
CERTIFICATE OF CORRECTION

PATENT NO. : 8,399,461 B2  
APPLICATION NO. : 12/513731  
DATED : March 19, 2013  
INVENTOR(S) : Himmelsbach et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this  
Third Day of September, 2013

Teresa Stanek Rea  
*Acting Director of the United States Patent and Trademark Office*